US011432707B2

(12) United States Patent
Akimoto et al.

(10) Patent No.: US 11,432,707 B2
(45) Date of Patent: Sep. 6, 2022

(54) ENDOSCOPE SYSTEM, PROCESSOR FOR ENDOSCOPE AND OPERATION METHOD FOR ENDOSCOPE SYSTEM FOR DETERMINING AN ERRONEOUS ESTIMATION PORTION

(71) Applicant: OLYMPUS CORPORATION, Tokyo (JP)

(72) Inventors: Shunya Akimoto, Nishitokyo (JP); Soichi Ikuma, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 517 days.

(21) Appl. No.: 16/713,319

(22) Filed: Dec. 13, 2019

(65) Prior Publication Data

US 2020/0154987 A1 May 21, 2020

Related U.S. Application Data

(63) Continuation of application No. PCT/JP2018/013155, filed on Mar. 29, 2018.

(30) Foreign Application Priority Data

Jun. 15, 2017 (JP) .............................. JP2017-117991

(51) Int. Cl.
*A61B 1/00* (2006.01)
*A61B 5/107* (2006.01)
(Continued)

(52) U.S. Cl.
CPC ...... *A61B 1/00193* (2013.01); *A61B 1/00009* (2013.01); *A61B 1/00045* (2013.01);
(Continued)

(58) Field of Classification Search
None
See application file for complete search history.

(56) References Cited

U.S. PATENT DOCUMENTS 6,683,985 B1 * 1/2004 Kase ....................... G06T 17/30
702/155
2009/0054729 A1 * 2/2009 Mori ....................... A61B 1/04
600/114

(Continued)

FOREIGN PATENT DOCUMENTS

CN 101389260 A 3/2009
CN 104755009 A 7/2015
(Continued)

OTHER PUBLICATIONS

International Search Report dated Jun. 5, 2018 received in PCT/JP2018/013155.

*Primary Examiner* — John P Leubecker
(74) *Attorney, Agent, or Firm* — Scully, Scott, Murphy & Presser, P.C.

(57) ABSTRACT

An endoscope system includes an endoscope that acquires an image of a subject and a processor. The processor acquires position and posture information of the endoscope, estimates a three-dimensional shape of the subject based on the image and the position and posture information, generates, based on the position information, a cross section crossing a trajectory on which the endoscope passed, and determines an erroneous estimation portion based on a shape characteristic of the three-dimensional shape on the cross section.

13 Claims, 18 Drawing Sheets

(51) Int. Cl.
  *G06T 7/00* (2017.01)
  *A61B 1/06* (2006.01)
  *G06T 17/30* (2006.01)

(52) U.S. Cl.
  CPC .......... *A61B 1/0669* (2013.01); *A61B 5/1076* (2013.01); *G06T 7/0012* (2013.01); *G06T 17/30* (2013.01); *G06T 2207/10068* (2013.01)

(56) References Cited

U.S. PATENT DOCUMENTS

| | | | |
|---|---|---|---|
| 2009/0073257 A1* | 3/2009 | Tanaka | G06T 7/0012 |
| | | | 348/E13.001 |
| 2012/0083696 A1 | 4/2012 | Kitamura | |
| 2013/0072805 A1 | 3/2013 | Schmitt et al. | |
| 2015/0196228 A1 | 7/2015 | Akimoto et al. | |
| 2018/0256017 A1 | 9/2018 | Inoue | |

FOREIGN PATENT DOCUMENTS

| | | |
|---|---|---|
| EP | 2 437 216 A1 | 4/2012 |
| JP | 2003-225195 A | 8/2003 |
| JP | 2009-213627 A | 9/2009 |
| JP | 2010-256988 A | 11/2010 |
| JP | 2012-075702 A | 4/2012 |
| JP | 5354494 B2 | 11/2013 |
| JP | 2017-012765 A | 1/2017 |
| WO | 2011/038044 A2 | 3/2011 |
| WO | 2017/057330 A1 | 4/2017 |
| WO | 2017/081821 A1 | 5/2017 |

\* cited by examiner

ENDOSCOPE SYSTEM, PROCESSOR FOR ENDOSCOPE AND OPERATION METHOD FOR ENDOSCOPE SYSTEM FOR DETERMINING AN ERRONEOUS ESTIMATION PORTION

CROSS REFERENCE TO RELATED APPLICATION

This application is a continuation application of PCT/JP2018/013155 filed on Mar. 29, 2018 and claims benefit of Japanese Application No. 2017-117991 filed in Japan on Jun. 15, 2017, the entire contents of which are incorporated herein by this reference.

BACKGROUND OF INVENTION

1. Field of the Invention

The present invention relates to an endoscope system that estimates a three-dimensional shape in a subject based on an image acquired by an endoscope and position information and posture information of the endoscope, a processor for endoscope, and an operation method for the endoscope system.

2. Description of the Related Art

There has been proposed an endoscope system that estimates a three-dimensional shape in a subject based on an image acquired by an endoscope and position information and posture information of the endoscope.

For example, Japanese Patent Application Laid-Open Publication No. 2003-225195 states that, in a monitor apparatus for a flexible endoscope in which bending-state displaying means for detecting a bending state of a flexible insertion section and causing a monitor screen to display the bending state is provided, organ-shape displaying means for causing the monitor screen to display a shape of an organ, which is an insertion target of the insertion section, together with the bending state of the insertion section and organ-shape correcting means for correcting, according to an external input, the shape of the organ displayed on the monitor screen are provided.

In Japanese Patent Application Laid-Open Publication No. 2009-213627, the following content is described. First, a doctor causes a patient to swallow a capsule endoscope (CE) and performs an endoscopic examination. The doctor selects CE image data (attention point image data) of an observed part (a point of attention) suspected of a lesion out of CE image data obtained by the CE. After the selection, the doctor selects CE image data of an observed part halfway in an endoscope insertion path leading from a mouth to the point of attention. When an endoscopic examination using a balloon endoscope (BE) is started, the doctor determines whether BE image data obtained by the BE and respective point image data selected by the doctor earlier are similar to each other. Consequently, by detecting which of respective points a distal end portion of the BE reaches, a relative position of the distal end portion is detected.

SUMMARY OF THE INVENTION

In the prior art documents, when a shape of an organ is estimated from an endoscopic image, first, positions of a point group configuring the shape of the organ are estimated. However, in general, errors are included in the estimated positions. When the shape of the organ is estimated from the point group, the estimated positions of which include the errors, a subject formed in a plane shape (a shape such as a plane or a curved surface) is sometimes estimated as, for example, a subject formed in a lumen shape. Therefore, it has been requested to reduce such erroneous estimation of a shape.

The present invention has been devised in view of the above circumstances, and an object of the present invention is to provide an endoscope system that can improve reliability of an estimated three-dimensional shape in a subject and an operation method for the endoscope system.

An endoscope system according to an aspect of the present invention includes: an endoscope that picks up an image in a subject and acquires the image; and a processor. The processor acquires position information and posture information of the endoscope, estimates, based on the image, a relative three-dimensional position viewed from the endoscope of a target portion in the subject, estimates a three-dimensional shape in the subject based on the relative three-dimensional position and the position information and the posture information, generates a cross section, which is a plane crossing a centerline of a region including a trajectory on which the endoscope passed, based on the position information, and determines an erroneous estimation portion in the three-dimensional shape based on a shape characteristic of a shape cross section, which is a portion crossing the cross section, of the three-dimensional shape.

A processor for endoscope according to an aspect of the present invention acquires position information and posture information of an endoscope, estimates, based on an image acquired by the endoscope, a relative three-dimensional position viewed from the endoscope of a target portion in a subject, estimates a three-dimensional shape in the subject based on the relative three-dimensional position and the position information and the posture information, generates a cross section, which is a plane crossing a centerline of a region including a trajectory on which the endoscope passed, based on the position information, and determines an erroneous estimation portion in the three-dimensional shape based on a shape characteristic of a shape cross section, which is a portion crossing the cross section, of the three-dimensional shape.

An operation method for an endoscope system according to an aspect of the present invention is an operation method for an endoscope system including an endoscope that picks up an image in a subject and acquires the image, the operation method including: acquiring position information and posture information of the endoscope; estimating, based on the image, a relative three-dimensional position viewed from the endoscope of a target portion in the subject; estimating a three-dimensional shape in the subject based on the relative three-dimensional position and the position information and the posture information; generating a cross section, which is a plane crossing a centerline of a region including a trajectory on which the endoscope passed, based on the position information; and determining an erroneous estimation portion in the three-dimensional shape based on a shape characteristic of a shape cross section, which is a portion crossing the cross section, of the three-dimensional shape.

DETAILED DESCRIPTION OF THE PREFERRED EMBODIMENTS

Embodiments of the present invention are explained below with reference to the drawings.

First Embodiment

Figure 1:
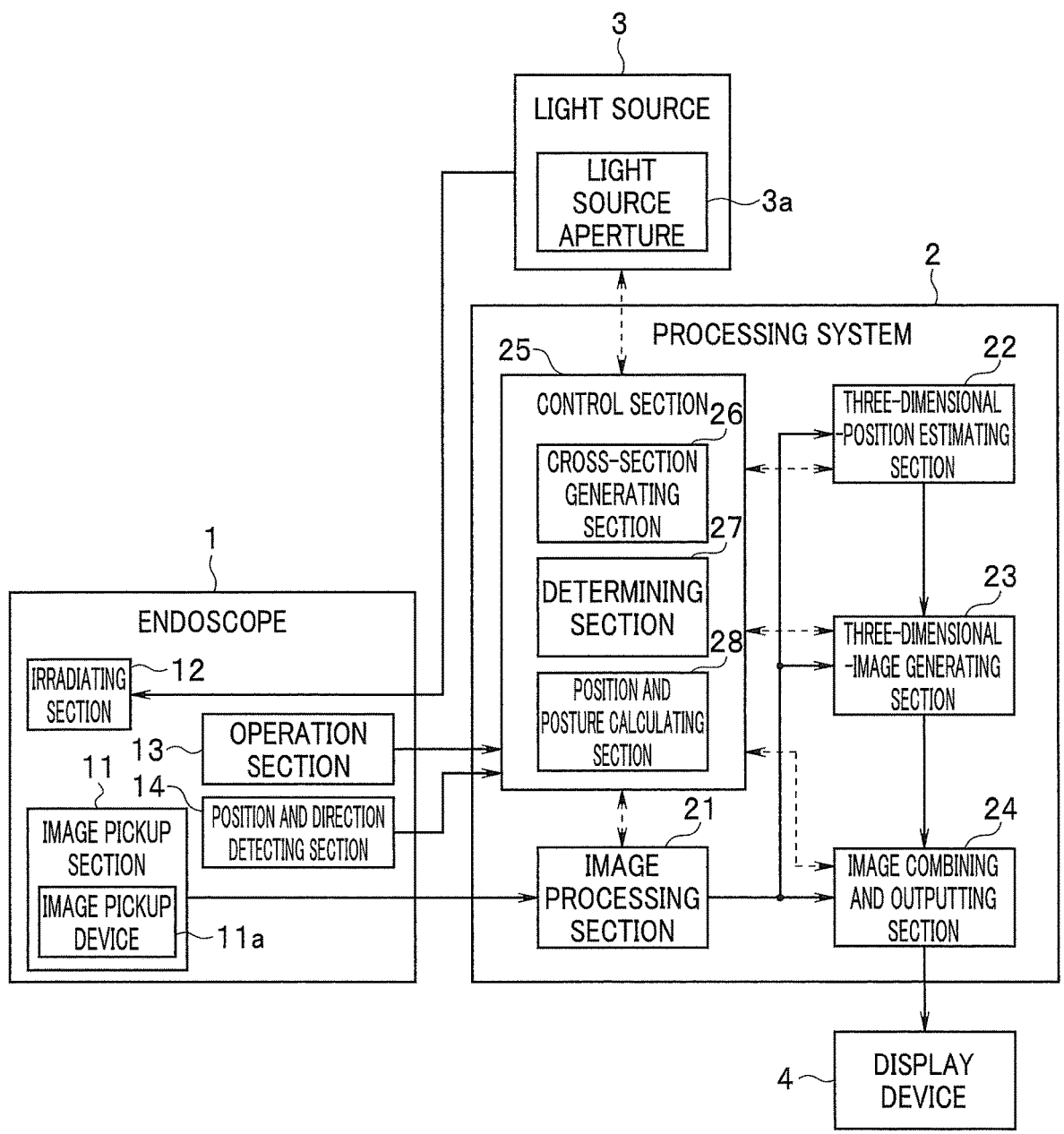
FIG. 1 is a block diagram showing a configuration of an endoscope system in a first embodiment of the present invention.

FIG. 1 to FIG. 12 show a first embodiment of the present invention. FIG. 1 is a block diagram showing a configuration of an endoscope system.

The endoscope system includes an endoscope 1, a processing system 2, a light source 3, and a display apparatus 4. Note that the processing system 2 and the light source 3 are separated in an example shown in FIG. 1. However, the processing system 2 and the light source 3 may be integrated.

The endoscope 1 is an image acquiring apparatus that picks up an image in a subject and acquires the image. The endoscope 1 includes an image pickup section 11, an irradiating section 12, an operation section 13, and a position and direction detecting section 14, which is a measuring section. Among these sections, the image pickup section 11, the irradiating section 12, and the position and direction detecting section 14 are disposed, for example, at a distal end portion of an insertion section of the endoscope 1. The operation section 13 is connected to a hand side of the insertion section.

Note that, in this embodiment, a renal pelvis (see FIG. 8 and the like) of a kidney is explained as an example of the subject. However, the present invention is not limited to this and can be widely applied to subjects that can be endoscopically observed.

The irradiating section 12 emits illumination light, which is transmitted from the light source 3 via, for example, a light guide, toward an inside of the subject. However, the irradiating section 12 may be configured as a light emitting source such as an LED. The illumination light may be emitted by electric power supplied from the light source 3.

The image pickup section 11 includes an image pickup device 11a. The image pickup section 11 forms, with an objective optical system, an optical image of the inside of the subject that is irradiated with the illumination light, performs photoelectric conversion with the image pickup device 11a to pick up an image, and generates and acquires the picked-up image.

The operation section 13 is a section for performing various kinds of operation relating to the endoscope 1 such as photographing of an image and, when a bending section is provided in the insertion section, bending operation of the bending section.

The position and direction detecting section 14 detects a position of the distal end portion of the insertion section of the endoscope 1 and outputs a position detection signal and detects a facing direction of the distal end portion of the insertion section of the endoscope 1 and outputs a direction detection signal. The position and direction detecting section 14 is configured to detect coordinates of three axes (x, y, and z axes), which are space coordinates, and angles around the three axes based on, for example, a magnetic field. The position and direction detecting section 14 is called 6D sensor or the like as well.

The processing system 2 controls the endoscope 1 and the light source 3 and processes a picked-up image acquired from the endoscope 1 and generates image data for display. Further, the processing system 2 is configured to estimate three-dimensional positions p (see FIG. 4 and the like) in the subject based on an acquired image, generate a three-dimensional image in the subject, for example, as a guide image based on the estimated three-dimensional positions p, and output the guide image to the display apparatus 4.

The processing system 2 includes an image processing section 21, a three-dimensional-position estimating section 22, a three-dimensional-image generating section 23, an image combining and outputting section 24, and a control section 25.

Note that the processing system 2 is configured to achieve functions of the respective sections in the processing system 2 by causing a processor including a CPU to execute software. However, the processing system 2 is not limited to this configuration. The processing system 2 may be configured by a processor including electronic circuits corresponding to the respective sections in the processing system 2. The processing system 2 may be configured by a processor including an integrated circuit such as an FPGA (field programmable gate array) including circuit sections corresponding to the respective sections in the processing system 2.

The image processing section 21 performs, on a picked-up image outputted from the image pickup section 11, various kinds of image processing such as synchronization processing (or demosaicking processing), white balance processing, color matrix processing, and gamma conversion processing and generates an endoscopic image.

The three-dimensional-position estimating section 22 estimates a relative three-dimensional position viewed from the endoscope 1 of a target portion in a subject 9 (see FIG. 4 and the like) based on an image (the picked-up image acquired by the image pickup device 11a or the endoscopic image processed by the image processing section 21).

More specifically, the three-dimensional-position estimating section 22 estimates, based on the image, a distance between the endoscope 1 and the subject, more specifically, a distance from a distal end portion (the distal end portion of the insertion section) of the endoscope 1 to a target portion of the subject.

Examples of a method with which the three-dimensional-position estimating section 22 estimates, based on the image, the distance from the distal end portion of the endoscope 1 to the target portion of the subject include the following method.

When it is assumed that light reflectances of respective parts of the subject are the same, return light that is emitted from the irradiating section 12 and reflected on the subject is darker as the distance from the distal end portion of the endoscope 1 is larger and, conversely, is brighter as the distance is smaller. Therefore, a distance to the target portion of the subject can be estimated according to luminance of an image (luminance of the target portion photographed in the image).

Note that the method of estimating the distance between the endoscope 1 and the subject based on the luminance of the image is explained above. However, a method of estimating the distance between the endoscope 1 and the subject is not limited to this. For example, when the endoscope 1 has a configuration including a plurality of image pickup sections having parallaxes, the distance between the endoscope 1 and the subject may be calculated based on a phase difference of a plurality of images obtained from the plurality of image pickup sections. Alternatively, the endoscope system may be configured to include a distance image sensor based on a pattern irradiation scheme, a TOF (time of flight) scheme, or the like to calculate the distance between the endoscope 1 and the subject.

The three-dimensional-position estimating section 22 estimates a relative three-dimensional position of the target portion viewed from a distal end of the endoscope 1 based on the estimated distance and a position of the target portion in the image (positions of pixels on which the target portion is photographed in the image).

A configuration of the objective optical system of the endoscope 1 is known. Information such as an angle of view is known in advance. At this time, a direction of the target portion viewed from the distal end portion of the endoscope 1 can be learned according to positions of pixels on which the target portion is photographed in an image acquired by the endoscope 1. Therefore, a distance and a direction of the target portion viewed from the distal end portion of the endoscope 1, that is, a relative three-dimensional position (a three-dimensional position in a relative coordinate system) of the target portion with respect to the endoscope 1 can be learned.

The three-dimensional-image generating section 23 generates a three-dimensional shape image corresponding to reliability based on control by the control section 25 using the relative three-dimensional position estimated by the three-dimensional-position estimating section 22.

Figure 3:
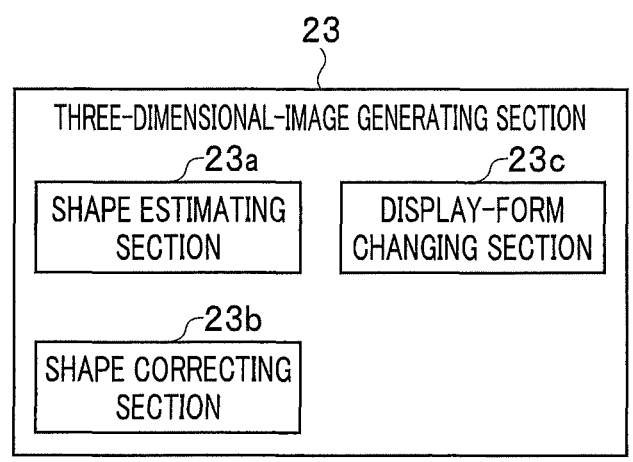
FIG. 3 is a block diagram showing a configuration of a three-dimensional-image generating section in the first embodiment.

FIG. 3 is a block diagram showing a configuration of the three-dimensional-image generating section 23.

The three-dimensional-image generating section 23 includes a shape estimating section 23a, a shape correcting section 23b, and a display-form changing section 23c.

Figure 2:
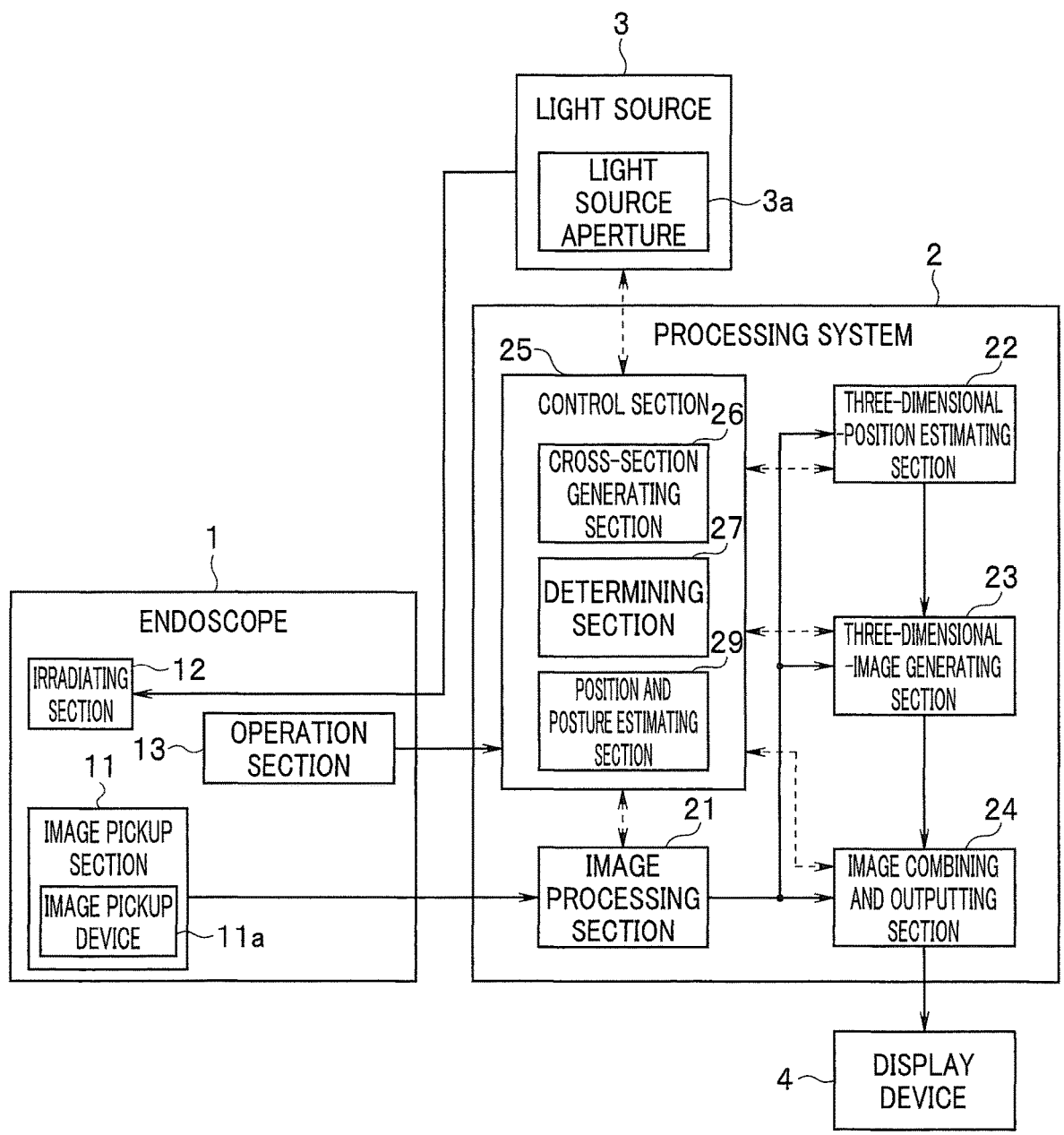
FIG. 2 is a block diagram showing a modification of the configuration of the endoscope system in the first embodiment.

The shape estimating section 23a estimates the three-dimensional positions p of the target portion in an absolute coordinate system in a treatment room or the like based on the relative three-dimensional position estimated by the three-dimensional-position estimating section 22 and the position information and the posture information of the endoscope 1 acquired by a position-posture-information acquiring section (the position and direction detecting section 14 and a position and posture calculating section 28 shown in FIG. 1 or a position and posture estimating section 29 shown in FIG. 2).

Further, the shape estimating section 23a estimates a three-dimensional shape 31 (see FIG. 4 and the like) in the subject 9 based on the three-dimensional positions p of the target portion (in general, the three-dimensional positions p are acquired concerning a plurality of points). More specifically, the shape estimating section 23a calculates a polygon 31p (see FIG. 10 and FIG. 11) based on the three-dimensional positions p of the target portion using a publicly-known method such as a ball-pivoting algorithm and generates a three-dimensional shape image configured by a plurality of polygons 31p (the three-dimensional shape image may indicate only a shape by connecting the plurality of polygons 31p or may be an image obtained by pasting an endoscopic image to the respective polygons 31p).

The shape correcting section 23b deletes, from the three-dimensional shape 31 estimated by the shape estimating section 23a, an erroneous estimation portion determined by a determining section 27 explained below (an erroneous estimation portion of the three-dimensional shape 31 estimated by the shape estimating section 23a).

As explained in a fourth embodiment below, the display-form changing section 23c displays the erroneous estimation portion determined by the determining section 27 in a display form, for example, a display color different from that of the other portions (portions not determined as the erroneous estimation portion) in the three-dimensional shape 31 estimated by the shape estimating section 23a.

Note that the display-form changing section 23c is not limited to functioning as a display-color changing section that changes the display color and only has to differentiate display forms in the erroneous estimation portion and the portions not determined as the erroneous estimation portion and enable distinction of the erroneous estimation portion and the other portions. For example, the display-form changing section 23c may differentiate luminances in the erroneous estimation portion and the portions not determined as the erroneous estimation portion or may add a specific pattern to the erroneous estimation portion.

For example, the shape correcting section 23b and the display-form changing section 23c alternatively function. When the erroneous estimation portion is deleted, the shape correcting section 23b functions and the display-form changing section 23c does not function. When the erroneous estimation portion is left without being deleted, the display-form changing section 23c functions and the shape correcting section 23b does not function.

For example, the image combining and outputting section 24 arranges the endoscopic image generated by the image processing section 21 and the three-dimensional shape image generated by the three-dimensional-image generating section 23 side by side and combines the endoscopic image and the three-dimensional shape image into one image and outputs the combined image to the display apparatus 4. Consequently, a user can insert and pull out the endoscope 1 while using the three-dimensional shape image as a guide via the display apparatus 4 and observe the inside of the subject with the endoscopic image and perform a test, treatment, and the like.

The control section 25 is connected to the image processing section 21, the three-dimensional-position estimating section 22, the three-dimensional-image generating section 23, and the image combining and outputting section 24 explained above. The control section 25 controls the entire processing system 2 and controls the endoscope 1 and controls on and off, a light amount, and the like of the light source 3 as well.

The control section 25 includes a cross-section generating section 26, a determining section 27, and a position and posture calculating section 28.

As explained below with reference to FIG. 8, the cross-section generating section 26 generates, based on position information of the endoscope 1, a cross section 32, which is a plane crossing (preferably, perpendicular to) a centerline 1c of a region 1a including a trajectory 1t on which the endoscope 1 passed.

The determining section 27 determines an erroneous estimation portion in the three-dimensional shape 31 based on a shape characteristic of a shape cross section 31c (see FIG. 8 and the like), which is a portion crossing the cross section 32, of the three-dimensional shape 31. The erroneous estimation portion is a portion where reliability is lower than a predetermined value in the three-dimensional shape 31. Therefore, the determining section 27 determines reliability of the three-dimensional shape 31.

The position and posture calculating section 28 generates position information and posture information of the distal end portion of the endoscope 1 based on the position detection signal and the direction detection signal detected by the position and direction detecting section 14. In other words, the position and direction detecting section 14 and the position and posture calculating section 28 configure a position-posture-information acquiring section that acquires position information and posture information of the endoscope 1.

The position information and the posture information of the endoscope 1 acquired by the position and posture calculating section 28 are outputted to the three-dimensional-image generating section 23. In this way, when estimating the three-dimensional positions p of the target portion in the absolute coordinate system from the relative three-dimensional position estimated by the three-dimensional-position estimating section 22, the shape estimating section 23a of the three-dimensional-image generating section 23 uses the position information and the posture information of the endoscope 1 acquired by the position and posture calculating section 28.

The light source 3 generates illumination light with which the subject is irradiated. The light source 3 includes a light source aperture 3a that controls a light amount of the illumination light by limiting a passage range of light.

The display apparatus 4 displays the image including the endoscopic image and the three-dimensional shape image outputted from the image combining and outputting section 24 such that the image can be observed.

FIG. 2 is a block diagram showing a modification of the configuration of the endoscope system.

In the modification shown in FIG. 2, instead of the position and direction detecting section 14 and the position and posture calculating section 28 shown in FIG. 1, a position and posture estimating section 29 is provided in the control section 25 of the processing system 2 as a position-posture-information acquiring section that acquires position information and posture information of the endoscope 1.

Besides a technique for detecting the position information and the posture information of the endoscope 1 with a sensor or the like, there has been known a technique for estimating the position information and the posture information of the endoscope 1 from an image or the like. Therefore, the position and posture estimating section 29 is configured to estimate a position and a posture of the endoscope 1 by performing an arithmetic operation or the like based on, for example, an image acquired by the endoscope 1 and acquire position information and posture information. The acquired position information and the acquired posture information of the endoscope 1 are used for the estimation of the three-dimensional positions p by the shape estimating section 23a as explained above.

Figure 4:
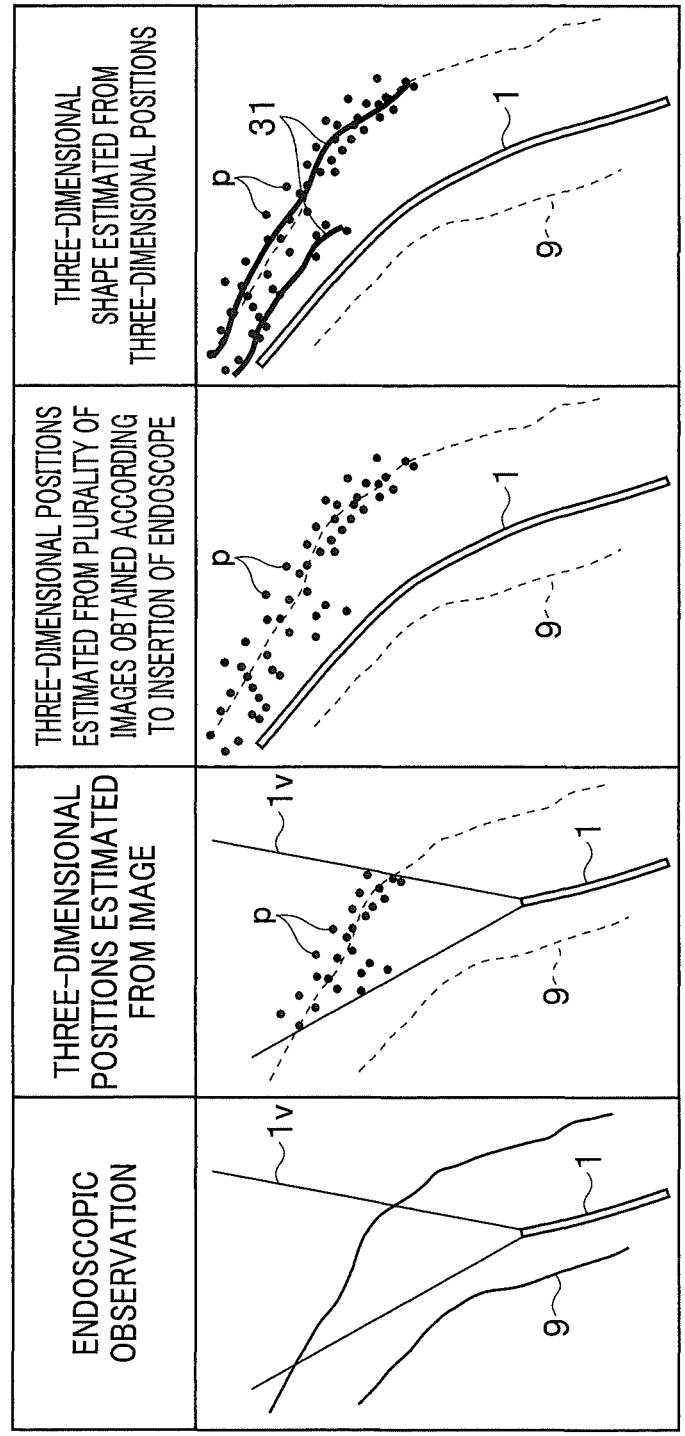
FIG. 4 is a diagram showing a state of performing observation while inserting an endoscope, estimating a three-dimensional position, and further estimating a three-dimensional shape in the first embodiment.

Subsequently, FIG. 4 is a diagram showing a state of performing observation while inserting the endoscope 1, estimating the three-dimensional positions p, and further estimating the three-dimensional shape 31. Note that, in FIG. 4, fields are referred to as a first field to a fourth field in order from the left to the right.

As shown in the first field of FIG. 4, the endoscope 1 has a field of vision 1v corresponding to a configuration of the objective optical system. An image of the subject 9 entering the field of vision 1v is acquired as an endoscopic image.

The three-dimensional-position estimating section 22 estimates a relative three-dimensional position based on the endoscopic image acquired in this way. The shape estimating section 23a of the three-dimensional-image generating section 23 estimates the three-dimensional positions p in the absolute coordinate based on the relative three-dimensional position. The three-dimensional positions p estimated in this way do not coincide with an actual position of the subject 9 as shown in the second field of FIG. 4. An error occurs in the three-dimensional positions p because of various factors.

By acquiring the endoscopic image and estimating the three-dimensional positions p while inserting the endoscope 1, as shown in the third field of FIG. 4, a plurality of kinds of information concerning the three-dimensional positions p estimated with respect to the subject 9 are collected.

The three-dimensional-image generating section 23 estimates the three-dimensional shape 31 based on the plurality of kinds of information concerning the three-dimensional positions p collected in this way. In an example shown in the fourth field of FIG. 4, the estimated three-dimensional shape 31 is estimated such that a wall section in the subject 9, which should be one curved surface, is formed as double structures at different distances (when stereoscopically seen, a structure of a false lumen shape near the wall section). An erroneous estimation portion occurs in the estimated three-dimensional shape 31.

Figure 5:
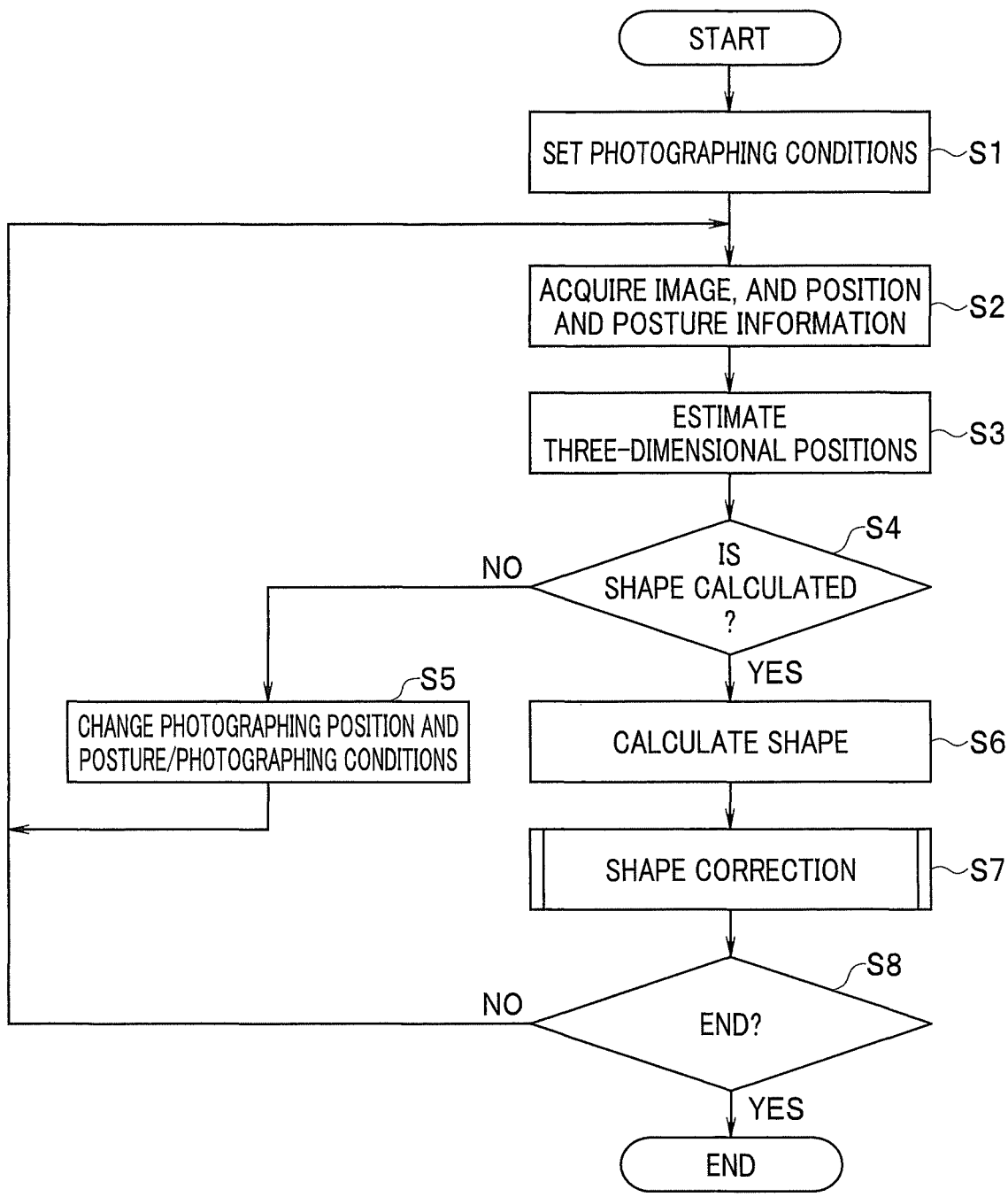
FIG. 5 is a flowchart showing action of the endoscope system in the first embodiment.

FIG. 5 is a flowchart showing action of the endoscope system.

When starting this processing, the endoscope system sets photographing conditions for acquiring an image, for example, a light source aperture value of the light source aperture 3a that controls a light amount of illumination light with which the subject is irradiated and a gain of the image pickup device 11a that acquires an image (step S1).

The endoscope system picks up and acquires an image with the image pickup device 11a and acquires, with the position and direction detecting section 14 and the position and posture calculating section 28 (or the position and posture estimating section 29), position information and posture information of the distal end portion of the endoscope 1 at a point in time when the image is acquired (step S2).

Then, the three-dimensional-position estimating section 22 and the shape estimating section 23a of the three-dimensional-image generating section 23 estimate the three-dimensional positions p based on the acquired image and the acquired position information and the acquired posture information (step S3).

Subsequently, the control section 25 determines whether to proceed to processing of shape calculation (step S4). For example, according to whether a predetermined number of images in which at least one of the position information and the posture information and the photographing conditions is different are acquired, the control section 25 determines whether to proceed to the processing of the shape calculation.

When it is determined not to proceed to the processing of the shape calculation yet, the endoscope system performs at least one of changing a photographing position and a posture by advancing or retracting the endoscope 1 in an inserting direction and changing the photographing conditions (step S5) and, then, returns to step S2 explained above and acquires the next image and the like, and performs the processing explained above.

When it is determined to proceed to the processing of the shape calculation in step S4 in this way, the shape estimating section 23a of the three-dimensional-image generating section 23 estimates, based on an estimated plurality of three-dimensional positions p, the three-dimensional shape 31 as a shape obtained by connecting a plurality of polygons 31p (step S6).

Further, the control section 25 determines whether to end this processing (step S8) after performing, on the estimated three-dimensional shape 31, processing of shape correction explained with reference to FIG. 6 below and displaying an image after the correction on the display apparatus 4 (step S7).

When it is determined not to end the processing yet, the endoscope system returns to step S2 and acquires the next image. When it is determined to end the processing, the endoscope system ends the processing.

Figure 6:
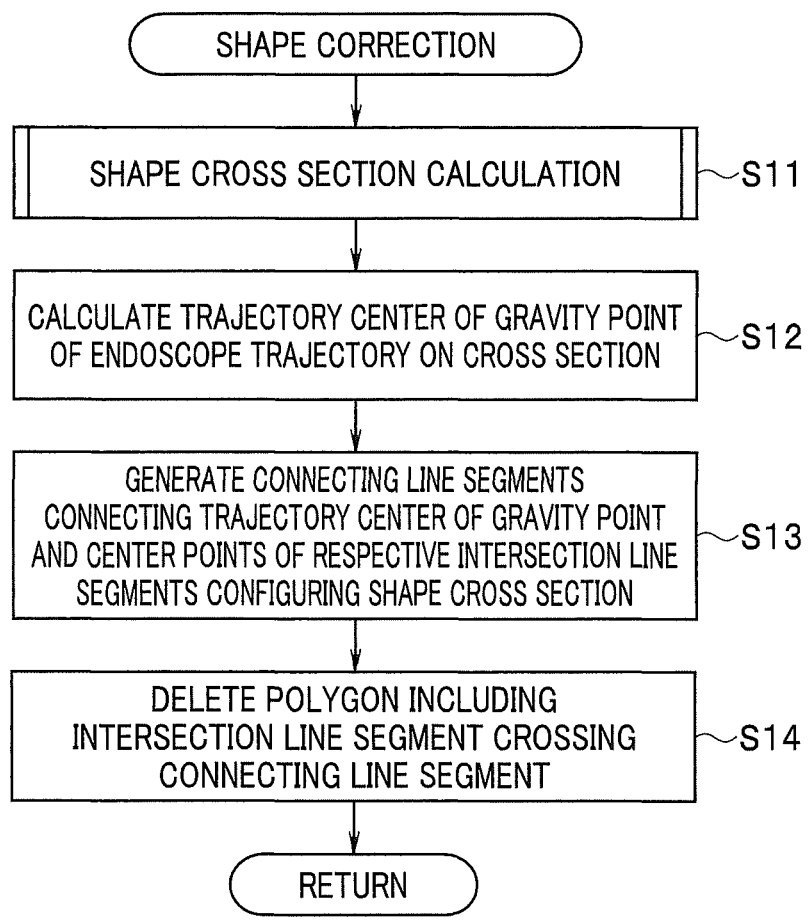
FIG. 6 is a flowchart showing processing of shape correction in the first embodiment.

FIG. 6 is a flowchart showing the processing of the shape correction in step S7 in FIG. 5.

When starting this processing, the endoscope system performs processing of shape cross section calculation (step S11).

Figure 7:
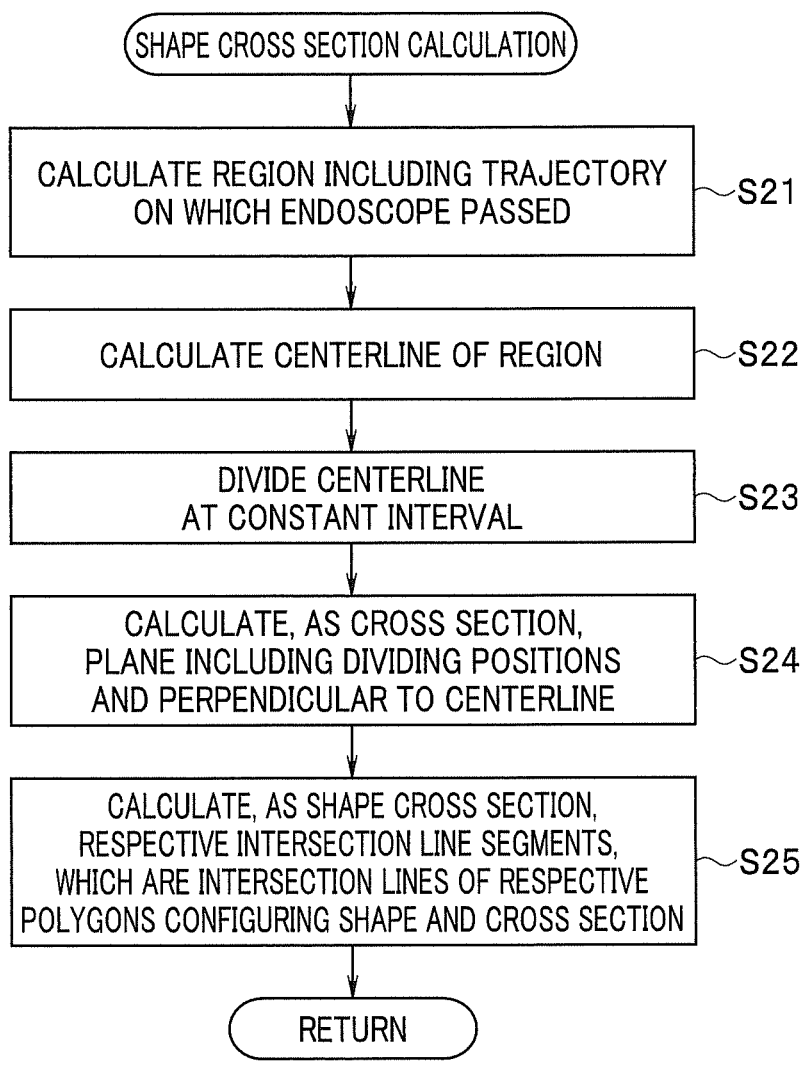
FIG. 7 is a flowchart showing processing of shape cross section calculation in the first embodiment.

FIG. 7 is a flowchart showing the processing of the shape cross section calculation in step S11 in FIG. 6. FIG. 8 is a diagram showing a state of calculating the centerline 1c of the region 1a including the trajectory 1t on which the endoscope 1 passed and further calculating the cross section 32 perpendicular to the centerline 1c. Note that, in FIG. 8, fields are referred to as first field to fourth field in order from the left to the right. Step numbers in FIG. 8 correspond to the step numbers in FIG. 5 and FIG. 7.

When the endoscope system enters the processing of the shape cross section calculation shown in FIG. 7, the cross-section generating section 26 calculates the trajectory 1t on which the endoscope 1 passed and further calculates the region 1a (see the second field in FIG. 8) including the trajectory 1t (step S21).

Figure 8:
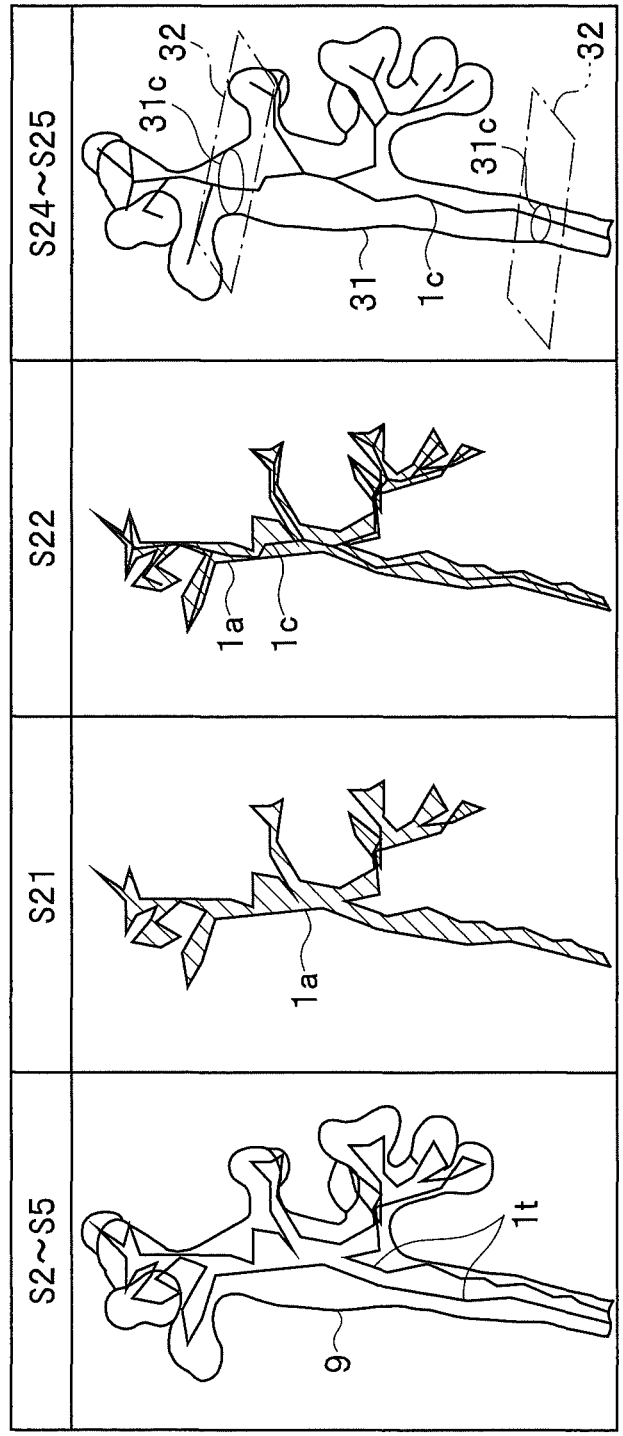
FIG. 8 is a diagram showing a state of calculating a centerline of a region including a trajectory on which the endoscope passed and further calculating a cross section perpendicular to the centerline in the first embodiment.

When the processing in steps S2 to S5 explained above is repeatedly performed, the distal end portion of the endoscope 1 moves and the trajectory 1t on which the distal end portion of the endoscope 1 passed shown in the first field of FIG. 8 is generated. The trajectory 1t can be learned based on the position information of the distal end portion of the endoscope 1 acquired by the position and direction detecting section 14 and the position and posture calculating section 28 (alternatively, the position and posture estimating section 29).

Subsequently, the cross-section generating section 26 calculates the centerline 1c of the region 1a shown in the third field of FIG. 8 (step S22) and divides the calculated centerline 1c at a constant interval (every constant length) (step S23).

The cross-section generating section 26 calculates, as the cross section 32 shown in the fourth field of FIG. 8, a plane including dividing positions of the centerline 1c and crossing the centerline 1c (in this embodiment, perpendicular to the centerline 1c) (step S24). Therefore, the cross-section generating section 26 generate a plurality of cross sections 32 perpendicular to the centerline 1c at every constant interval along the centerline 1c.

Further, the cross-section generating section 26 calculates, as the shape cross section 31c, respective intersection line segments 31s, which are intersection lines of the respective polygons 31p configuring the three-dimensional shape 31 and the cross section 32 (step S25).

Figure 9:
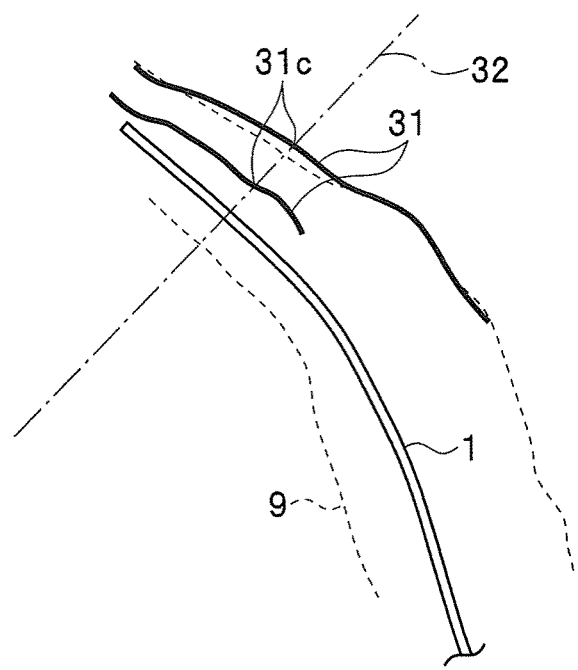
FIG. 9 is a diagram showing an example of a positional relation between the estimated three-dimensional shape and the cross section perpendicular to the centerline in the first embodiment.

FIG. 9 is a diagram showing an example of a positional relation between the estimated three-dimensional shape 31 and the cross section 32 perpendicular to the centerline 1c.

The shape cross section 31c is the portion of the three-dimensional shape 31 crossing the cross section 32 as explained above.

Figure 10:
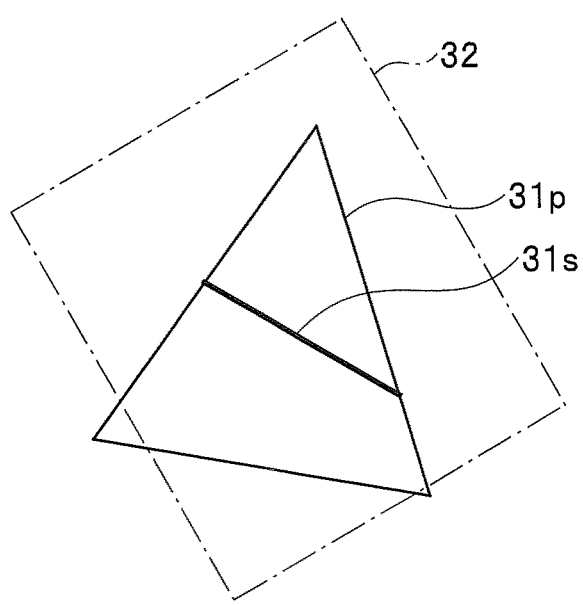
FIG. 10 is a diagram showing an intersection line segment, which is an intersection line of the cross section perpendicular to the centerline and one polygon in the first embodiment.

FIG. 10 is a diagram showing the intersection line segment 31s, which is an intersection line of the cross section 32 perpendicular to the centerline 1c and one polygon 31p. Since the polygon 31p is a plane formed in a polygonal shape, the intersection line segment 31s is a line segment formed in a straight line. Therefore, the shape cross section 31c is formed in a polygonal line obtained by connecting a plurality of intersection line segments 31s, which are intersection lines of the cross section 32 and the polygons 31p.

After performing the processing in step S25 in this way, the endoscope system returns to the processing shown in FIG. 6.

When the shape cross section 31c is calculated in step S11 in FIG. 6, the determining section 27 calculates a trajectory point Pt (see FIG. 17 and the like), which is an intersection of the cross section 32 and the trajectory 1t of the endoscope 1 and further calculates a trajectory center of gravity point Gt (see FIG. 11, FIG. 12, and the like), which is a center of gravity point of the trajectory point Pt (step S12).

Note that, since an endoscopic observation is performed while advancing and retracting the endoscope 1, it is expected that a plurality of trajectory points Pt are present (therefore, the trajectory center of gravity point Gt is calculated as a center of gravity point of the plurality of trajectory points Pt). However, if one trajectory point Pt is present on the cross section 32, the one trajectory point Pt is the trajectory center of gravity point Gt.

The determining section 27 generates, respectively for the respective intersection line segments 31s configuring the shape cross section 31c, connecting line segments 33 connecting the trajectory center of gravity point Gt and center points 31a, which are midpoints of the intersection line segments 31s (step S13).

Figure 11:
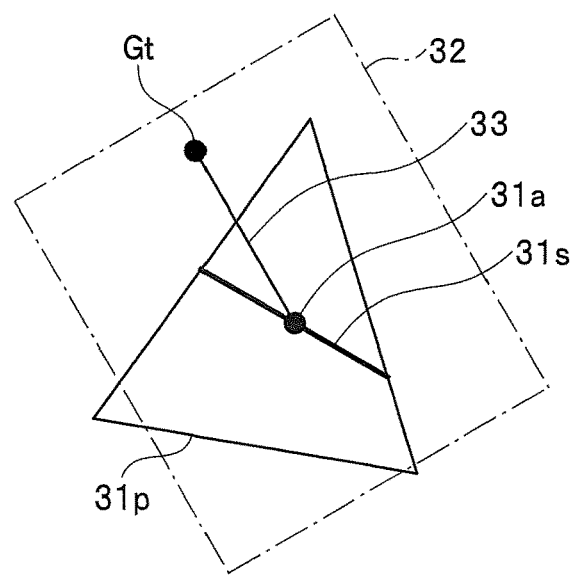
FIG. 11 is a diagram showing a state of generating a connecting line segment connecting a center point of the intersection line segment and a trajectory center of gravity point on the cross section perpendicular to the centerline in the first embodiment.
Figure 12:
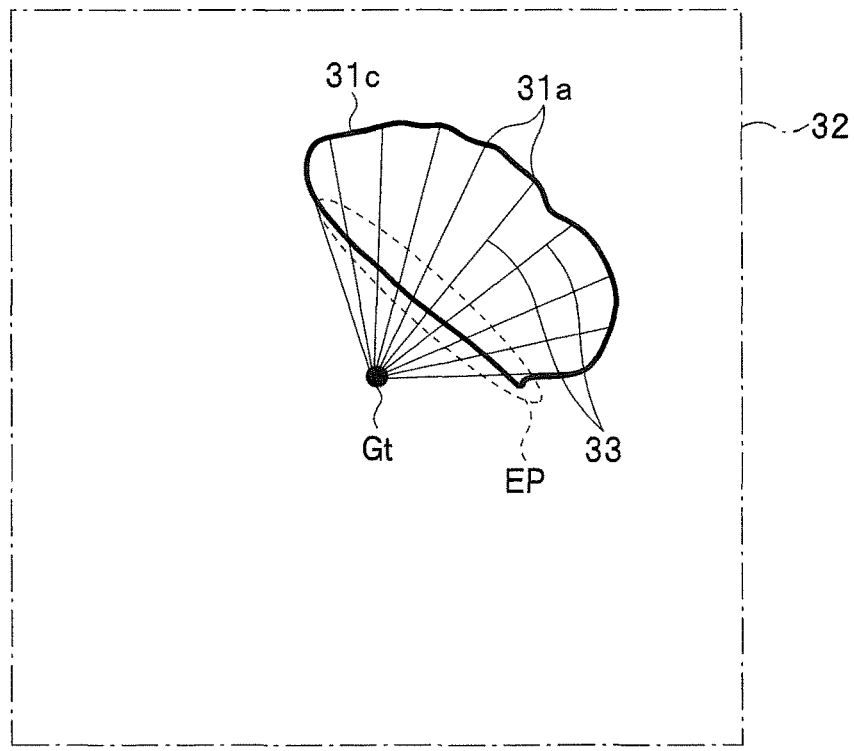
FIG. 12 is a diagram showing intersection line segments of a shape cross section crossing connecting line segments in the first embodiment.

FIG. 11 is a diagram showing a state of generating the connecting line segment 33 connecting the center point 31a of the intersection line segment 31s and the trajectory center of gravity point Gt on the cross section 32 perpendicular to the centerline 1c. When processing for generating the connecting line segment 33 is performed on the respective intersection line segments 31s configuring the shape cross section 31c, for example, a plurality of connecting line segments 33 shown in FIG. 12 are obtained. FIG. 12 is a diagram showing the intersection line segments 31s of the shape cross section 31c crossing the connecting line segments 33.

An example shown in FIG. 12 shows a state in which the cross section 32 is present in the portion of the three-dimensional shape 31 that should have a plane shape but is erroneously estimated as a lumen shape as shown in FIG. 9. The determining section 27 determines, based on the intersection line segment 31s, whether the polygon 31p including the intersection line segment 31s is an erroneous estimation portion. In the example shown in FIG. 12, the intersection line segment 31s of the shape cross section 31c present in a region EP surrounded by a dotted line crosses the connecting line segment 33. Therefore, the determining section 27 in this embodiment determines that the polygon 31p including the intersection line segment 31s crossing the connecting line segment 33 (the polygon 31p, the intersection line segment 31s of which is present in the region EP) as shown in FIG. 12 is an erroneous estimation portion.

In other words, the determining section 27 generates, with respect to each of the plurality of intersection line segments 31s, the connecting line segment 33 having, as both ends, the trajectory point Pt, which is an intersection of the cross section 32 and the trajectory 1t, and the center point 31a of the intersection line segment 31s and determines, as an erroneous estimation portion, the polygon 31p including the intersection line segment 31s crossing the connecting line segment 33 in a part other than both the ends of the connecting line segment 33.

At this time, when a plurality of trajectory points Pt are present on one cross section 32, the determining section 27 generates the connecting line segment 33 with one end set at the trajectory center of gravity point Gt, which is a center of gravity of the plurality of trajectory points Pt, and determines an erroneous estimation portion.

The shape correcting section 23b in the three-dimensional-image generating section 23 deletes the polygon 31p including the intersection line segment 31s crossing the connecting line segment 33 (the polygon 31p, the intersection line segment 31s of which is present in the region EP), the polygon 31p being determined as the erroneous estimation portion by the determining section 27 (step S14). Note that, although the erroneous estimation portion is deleted by the shape correcting section 23b, instead, the display form of the erroneous estimation portion may be changed by the display-form changing section 23c as explained above.

After performing the processing in step S14 in this way, the endoscope system returns to the processing shown in FIG. 5.

According to such a first embodiment, the cross section 32 crossing the centerline 1c of the region 1a including the trajectory 1t on which the endoscope 1 passed is generated. An erroneous estimation portion in the three-dimensional shape 31 is determined based on the shape characteristic of the shape cross section 31c, which is the portion crossing the cross section 32 of the three-dimensional shape 31. Therefore, it is possible to, for example, delete the erroneous estimation portion and correct the three-dimensional shape 31 or display the erroneous estimation portion of the three-dimensional shape 31 to enable the user to identify the erroneous estimation portion. It is possible to improve reliability of the estimated three-dimensional shape 31 in the subject.

When the three-dimensional shape 31 is estimated as a shape obtained by connecting a plurality of polygons 31p, it is possible to effectively use a publicly-known algorithm such as the ball-pivoting algorithm explained above.

It is possible to perform processing with a light load within a two-dimensional plane by determining, based on the intersection line segment 31s, which is the intersection line of the cross section 32 and the polygon 31p, whether the polygon 31p including the intersection line segment 31s is an erroneous estimation portion.

Further, the connecting line segment 33 having, as the both ends, the trajectory point Pt, which is the intersection of the cross section 32 and the trajectory 1t of the endoscope 1, and the center point 31a of the intersection line segment 31s are generated with respect to each of the plurality of intersection line segments 31s. The polygon 31p including the intersection line segment 31s crossing the connecting line segment 33 in a part other than both the ends of the connecting line segment 33 is determined as an erroneous estimation portion. Therefore, an erroneous estimation portion in the three-dimensional shape 31 that should be have a plane shape but is erroneously estimated as a lumen shape can be appropriately determined.

In addition, when the plurality of trajectory points Pt are present on one cross section 32, the connecting line segment 33 is generated with one end set at the trajectory center of gravity point Gt, which is the center of gravity of the plurality of trajectory points Pt, and the determination of an erroneous estimation portion is performed. Therefore, it is possible to obtain an appropriate result while reducing a processing load than when the connecting line segment 33 is generated with one end set at each of the plurality of trajectory points Pt.

The plurality of cross sections 32 perpendicular to the centerline 1c are generated at every constant interval along the centerline 1c. Therefore, it is possible to appropriately extract a polygon that is an erroneous estimation portion.

Further, since the determined erroneous estimation portion is deleted from the three-dimensional shape 31, it is possible to perform more appropriate observation of an image of the three-dimensional shape 31. On the other hand, when the display form of the erroneous estimation portion is changed, the user can recognize the erroneous estimation portion at a glance.

Second Embodiment

Figure 13:
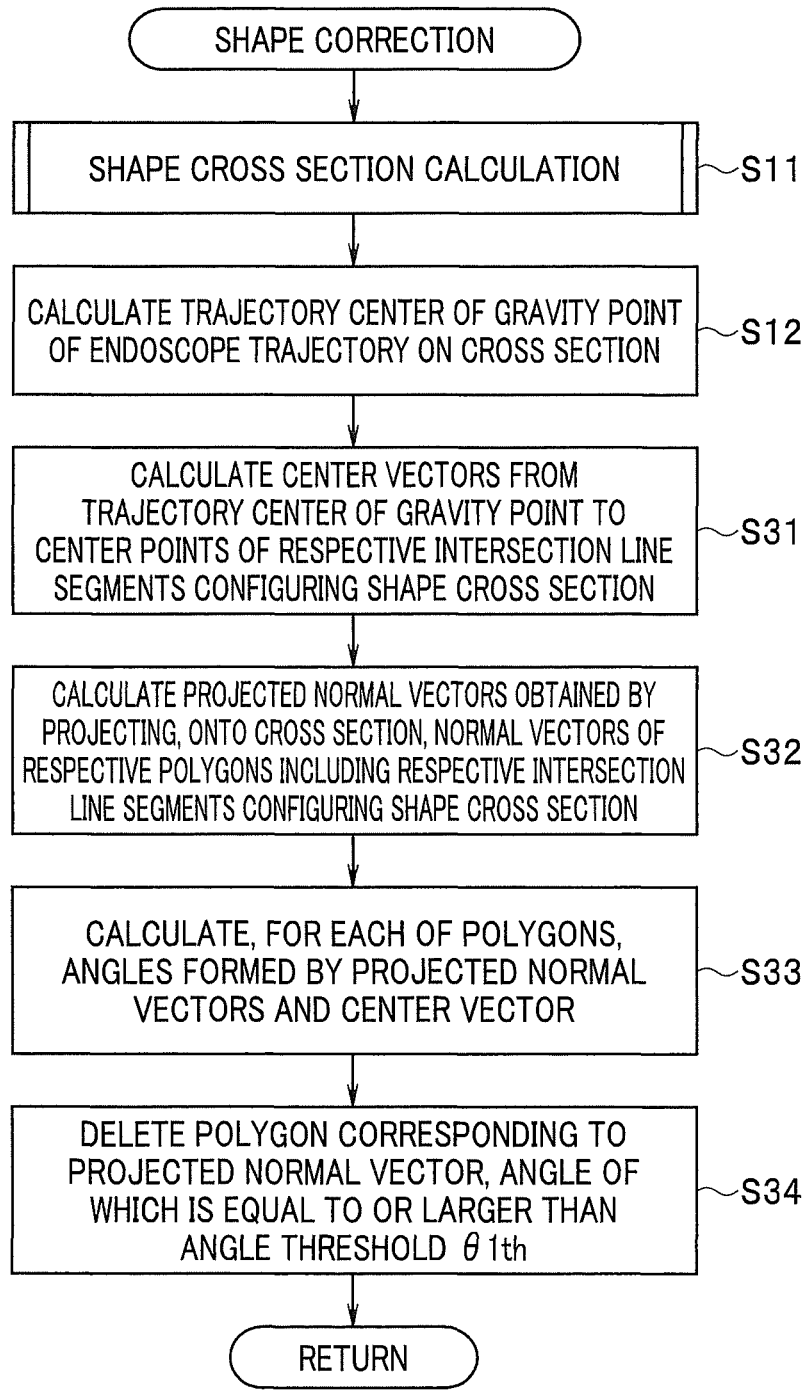
FIG. 13 is a flowchart showing processing of shape correction in a second embodiment of the present invention.
Figure 14:
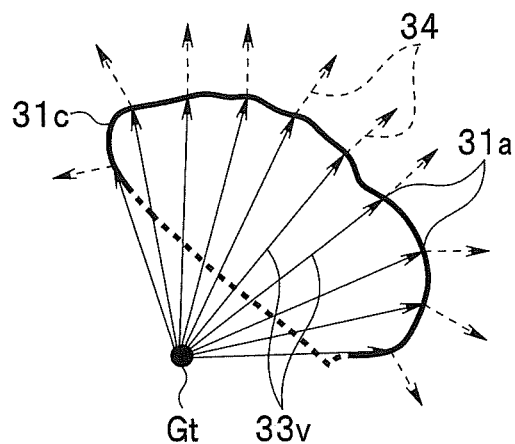
FIG. 14 is a diagram showing an example in which an angle formed by center vectors from a trajectory center of gravity point to center points of respective intersection line segments and projected normal vectors obtained by projecting, onto a cross section, normal vectors of respective polygons including the respective intersection line segments is smaller than an angle threshold in the second embodiment.
Figure 15:
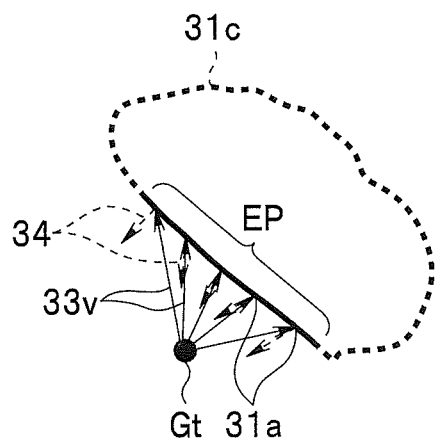
FIG. 15 is a diagram showing an example in which an angle formed by the center vectors and the projected normal vectors is equal to or larger than the angle threshold in the second embodiment.

FIG. 13 to FIG. 15 show a second embodiment of the present invention. FIG. 13 is a flowchart showing processing of shape correction.

In the second embodiment, the same portions as the portions in the first embodiment explained above are denoted by the same reference numerals and signs and explanation of the portions is omitted as appropriate. Only differences are mainly explained.

A configuration and basic action of an endoscope system in this embodiment are the same as those in the first embodiment explained above. However, in this embodiment, a determination method for an erroneous estimation portion is differentiated from that in the first embodiment explained above.

When entering processing shown in FIG. 13 in step S7 in FIG. 5, the endoscope system calculates the shape cross section 31c in step S11 and calculates the trajectory center of gravity point Gt in step S12.

Subsequently, the determining section 27 generates, with respect to each of the plurality of intersection line segments 31s, center vectors 33v (see FIG. 14, FIG. 15, and the like) from the trajectory center of gravity point Gt, which is the center of gravity of the trajectory point Pt, which is the intersection of the cross section 32 and the trajectory 1t, to the center points 31a of the intersection line segments 31s (step S31).

Further, the determining section 27 generates, with respect to each of the polygons 31p including the intersection line segments 31s, projected normal vectors 34 (see FIG. 14, FIG. 15, and the like) obtained by projecting, onto the cross section 32, normal vectors of the respective polygons 31p including the respective intersection line segments 31s configuring the shape cross section 31c (step S32). Note that it is assumed that directions are given to the projected normal vectors 34 toward an outer diameter direction of the shape cross section 31c formed in a closed curve shown in FIG. 14 and FIG. 15.

The determining section 27 calculates, for each of the polygons 31p, angles formed by the center vectors 33v and the projected normal vectors 34 (step S33).

FIG. 14 is a diagram showing an example in which an angle formed by the center vectors 33v from the trajectory center of gravity point Gt to the center points 31a of the respective intersection line segments 31s and the projected normal vectors 34 obtained by projecting, onto the cross section 32, the normal vectors of the respective polygons 31p including the respective intersection line segments 31s is smaller than an angle threshold θ1th.

On the other hand, FIG. 15 is a diagram showing an example in which the angle formed by the center vectors 33v and the projected normal vectors 34 is equal to or larger than the angle threshold θ1th.

The determining section 27 determines, as an erroneous estimation portion, the polygon 31p including the intersection line segment 31s in which the angle formed by the center vector 33v and the projected normal vector 34 is equal to or larger than the angle threshold θ1th as shown in the region EP of FIG. 15. The shape correcting section 23b in the three-dimensional-image generating section 23 deletes the polygon 31p determined as the erroneous estimation portion by the determining section 27 (the polygon 31p, the intersection line segment 31s of which is present in the region EP) (step S34).

After performing the processing in step S34 in this way, the endoscope system returns to the processing shown in FIG. 5.

According to such a second embodiment, substantially the same effects as the effects in the first embodiment explained above are achieved. Further, the polygon 31p including the intersection line segment 31s in which the angle formed by the center vector 33v from the trajectory center of gravity point Gt to the center point 31a of the intersection line segment 31s and the projected normal vector 34 obtained by projecting the normal vector of the polygon 31p onto the cross section 32 is equal to or larger than the angle threshold θ1th is determined as the erroneous estimation portion. Therefore, it is possible to perform simple processing by a vector operation.

Third Embodiment

Figure 16:
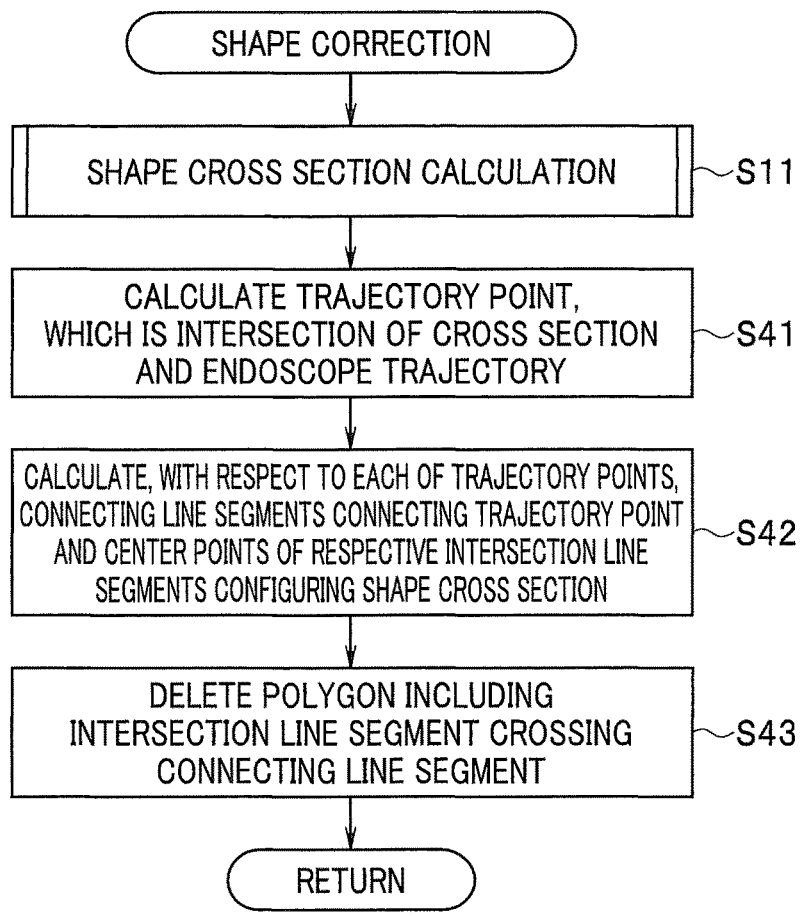
FIG. 16 is a flowchart showing processing of shape correction in a third embodiment of the present invention.
Figure 17:
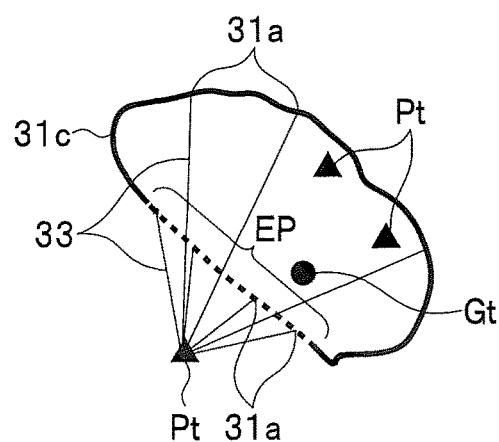
FIG. 17 is a diagram showing a state of calculating connecting line segments connecting a trajectory point that is an intersection of a cross section and a trajectory of an endoscope, and center points of intersection line segments, the calculated connecting line segments crossing the intersection line segments of a shape cross section in the third embodiment.

FIG. 16 and FIG. 17 show a third embodiment of the present invention. FIG. 16 is a flowchart showing processing of shape correction.

In the third embodiment, the same portions as the portions in the first and second embodiments explained above are denoted by the same reference numerals and signs and explanation of the portions is omitted as appropriate. Only differences are mainly explained.

A configuration and basic action of an endoscope system in this embodiment are the same as those in the first embodiment explained above. However, in this embodiment, a determination method for an erroneous estimation portion is differentiated from that in the first embodiment explained above.

When entering processing shown in FIG. 16 in step S7 in FIG. 5, the endoscope system calculates the shape cross section 31c in step S11.

Subsequently, the determining section 27 calculates the trajectory point Pt, which is an intersection of the cross section 32 and the trajectory 1t of the endoscope 1 (step S41).

When a plurality of trajectory points Pt are present on one cross section 32, the determining section 27 calculates, with respect to each of the plurality of trajectory points Pt, the connecting line segments 33 connecting the trajectory point Pt and the center points 31*a* of the respective intersection line segments 31*s* configuring the shape cross section 31*c* (step S42).

Subsequently, the determining section 27 determines, as an erroneous estimation portion, the polygon 31*p* including the intersection line segment 31*s* crossing the connecting line segment 33 as shown in the region EP in FIG. 17. Thereafter, the shape correcting section 23*b* in the three-dimensional-image generating section 23 deletes the polygon 31*p* determined as the erroneous estimation portion by the determining section 27 (the polygon 31*p*, the intersection line segment 31*s* of which is present in the region EP) (step S43).

After performing the processing in step S43 in this way, the endoscope system returns to the processing shown in FIG. 5.

FIG. 17 is a diagram showing a state of calculating the connecting line segments 33 connecting the trajectory point Pt, which is an intersection of the cross section 32 and the trajectory 1*t* of the endoscope 1, and the center points 31*a* of the intersection line segments 31*s*, the calculated connecting line segments 33 crossing the intersection line segments 31*s* of the shape cross section 31*c*.

In an example shown in FIG. 17, three trajectory points Pt are present. The trajectory center of gravity point Gt is present on an inside of the shape cross section 31*c*. In such a case, the connecting line segment 33 having the trajectory center of gravity point Gt at one end does not cross the intersection line segment 31*s*. In the operation in the first embodiment explained above, it is determined that an erroneous estimation portion is absent.

On the other hand, if at least one of the three trajectory points Pt is present on an outside of the shape cross section 31*c* that forms a closed curve, the connecting line segment 33 connecting the trajectory point Pt present on the outside of the shape cross section 31*c* and the center point 31*a* of the intersection line segment 31*s* crosses, in a part other than both the ends, the intersection line segment 31*s* configuring any part of the shape cross section 31*c*.

According to such a third embodiment, substantially the same effects as the effects in the first embodiment explained above are achieved. Further, when the plurality of trajectory points Pt are present on one cross section 32, the connecting line segments 33 are generated with respect to each of the plurality of trajectory points Pt and determination of an erroneous estimation portion is performed. Therefore, even when the trajectory center of gravity points Gt is present on the inside of the shape cross section 31*c*, it is possible to appropriately determine an erroneous estimation portion.

Note that the determination method may be switched as appropriate according to positions of the trajectory center of gravity point Gt and the trajectory point Pt in such a manner as to calculate, for each of respective cross sections, a line segment connecting the trajectory center of gravity point Gt and the trajectory point Pt and use the determination method in the third embodiment when the calculated line segment crosses the intersection line segment 31*s* and use the determination method in the first embodiment when the calculated line segment does not cross the intersection line segment 31*s*.

Fourth Embodiment

Figure 18:
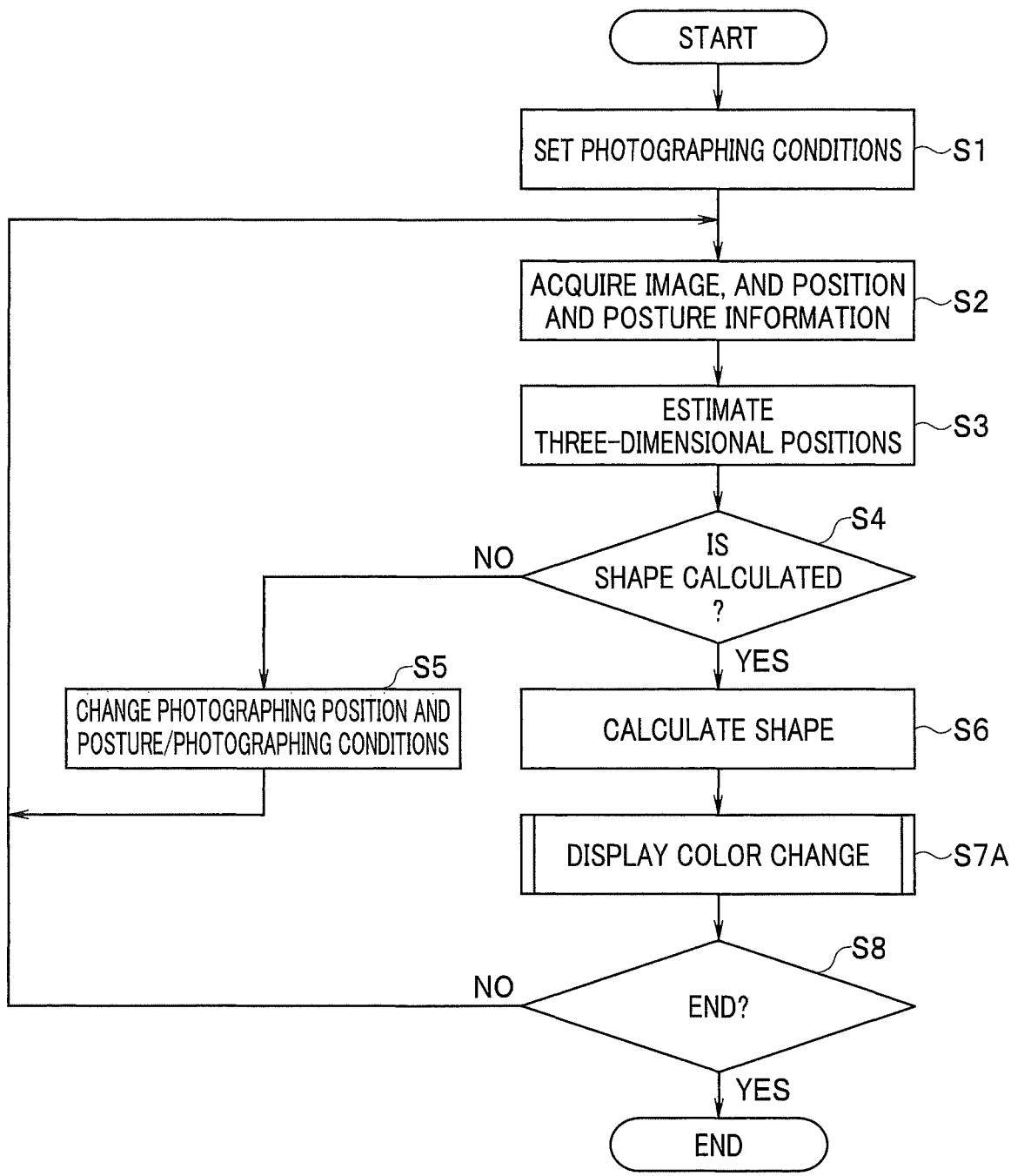
FIG. 18 is a flowchart showing action of an endoscope system in a fourth embodiment of the present invention.

FIG. 18 to FIG. 21 show a fourth embodiment of the present invention. FIG. 18 is a flowchart showing action of an endoscope system.

In the fourth embodiment, the same portions as the portions in the first to third embodiments explained above are denoted by the same reference numerals and signs and explanation of the portions is omitted as appropriate. Only differences are mainly explained.

A configuration and basic action of an endoscope system in this embodiment are the same as those in the first embodiment explained above. However, in this embodiment, a determination method for an erroneous estimation portion is differentiated from that in the first embodiment explained above.

In the first to third embodiments explained above, the deletion of the polygon 31*p* determined as the erroneous estimation portion is mainly explained. However, in this embodiment, instead of deleting the polygon 31*p*, a display form, for example, a display color of the polygon 31*p* is changed.

When starting processing of the endoscope system shown in FIG. 18, the endoscope system performs the processing in steps S1 to S4 explained above and performs the processing in step S5 or step S6 according to a determination result in step S4.

After performing the processing in step S6, the endoscope system performs processing of a display color change explained with reference to FIG. 19 and displays, on the display apparatus 4, an image in which a display color of an erroneous estimation portion is changed (step S7A). Then, in step S8, the control section 25 determines whether to end this processing. When the control section 25 determines not to end the processing, the endoscope system returns to step S2 and acquires the next image. When the control section 25 determines to end the processing, the endoscope system ends this processing.

Figure 19:
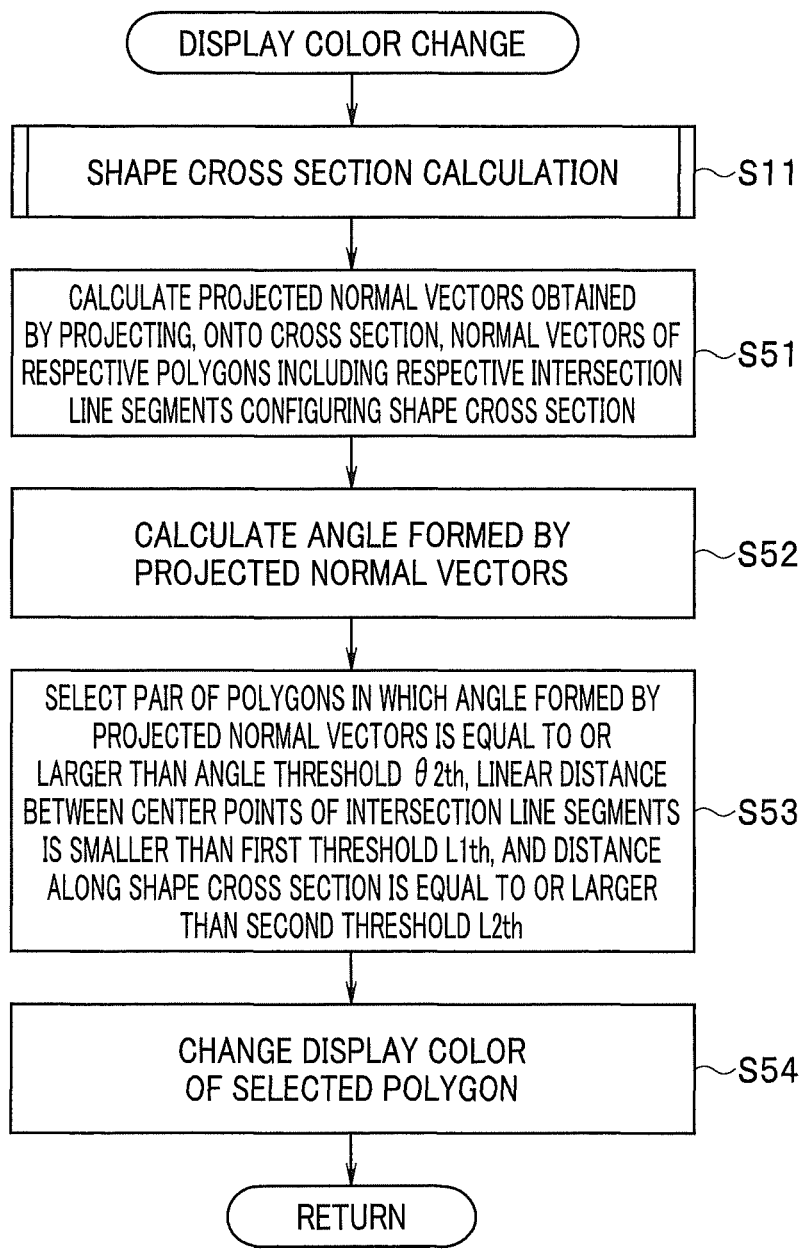
FIG. 19 is a flowchart showing processing of a display color change in the fourth embodiment.

FIG. 19 is a flowchart showing the processing of the display color change in step S7A in FIG. 18.

When starting this processing, in step S11, the endoscope system calculates the shape cross section 31*c*.

Subsequently, the determining section 27 generates, with respect to each of the polygons 31*p* including the intersection line segments 31*s*, the projected normal vectors 34 (see FIG. 20) obtained by projecting, onto the cross section 32, normal vectors of the respective polygons 31*p* including the respective intersection line segments 31*s* configuring the shape cross section 31*c* (step S51).

Subsequently, the determining section 27 calculates, with respect to all combinations of a pair of polygons 31*p* in a plurality of polygons 31*p*, an angle formed by the projected normal vectors 34 (step S52).

Further, the determining section 27 determines, as an erroneous estimation portion, a pair of polygons 31*p* in which an angle formed by the projected normal vectors 34 is equal to or larger than an angle threshold $\theta 2th$, a linear distance between the center points 31*a* of the intersection line segments 31*s* is smaller than a first threshold L1*th*, and a distance along the shape cross section 31*c* between the center points 31*a* of the intersection line segments 31*s* is equal to or larger than a second threshold L2*th* that is larger than the first threshold L1*th*.

Note that both of the first threshold L1*th* and the second threshold L2*th* are positive values. The second threshold L2*th* is, for example, a half or less of a total distance along the shape cross section 31*c* (a distance around the shape cross section 31*c*).

Figure 20:
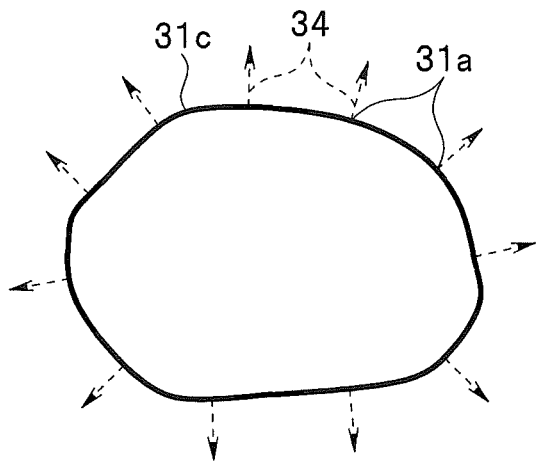
FIG. 20 is a diagram showing an example in which it is determined that erroneous estimation of a shape is absent in determination based on an angle formed by projected normal vectors, a linear distance between center points, and a distance along a shape cross section between the center points in the fourth embodiment.
Figure 21:
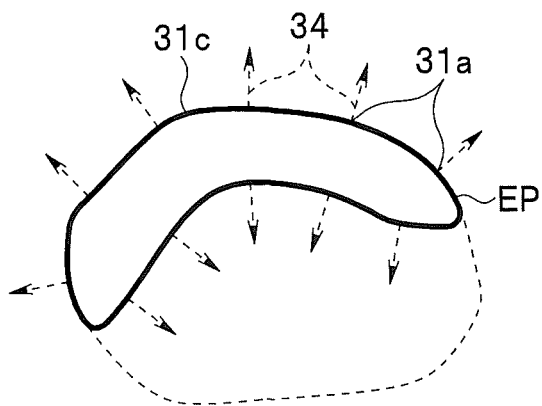
FIG. 21 is a diagram showing an example in which erroneous estimation of a shape is present in the determination based on the angle formed by the projected normal vectors, the linear distance between the center points, and the distance along the shape cross section between the center points in the fourth embodiment.

FIG. 20 is a diagram showing an example in which it is determined that erroneous estimation of a shape is absent in determination based on an angle formed by the projected normal vectors 34, a linear distance between the center points 31a, and a distance along the shape cross section 31c between the center points 31a. FIG. 21 is a diagram showing an example in which erroneous estimation of a shape is present in the determination based on the angle formed by the projected normal vectors 34, the linear distance between the center points 31a, and the distance along the shape cross section 31c between the center points 31a.

The three-dimensional shape 31, which should be a plane shape, is erroneously estimated as a lumen shape because of, for example, an estimation error in estimating a distance from the distal end portion of the endoscope 1 to the target portion of the subject. In general, this estimation error is expected to be smaller than a distance from the distal end portion of the endoscope 1 to the target portion of the subject (that is, a measurement error is smaller than a measurement value). Therefore, in this case, the estimated three-dimensional shape 31 is close to an actual shape of the subject 9.

In other words, compared with a case shown in FIG. 20 in which it is determined that an erroneous estimation portion is absent, in a case shown in FIG. 21 in which it is determined that an erroneous estimation portion is present, in the shape cross section 31c formed in a closed curve, a place close to a linear distance is considered to be present in an opposite side portion in a distance along the shape cross section 31c. In the place close to the linear distance, the projected normal vector 34 is considered to be in a substantially opposite direction.

Therefore, in this embodiment, determination of an erroneous estimation portion is performed by integrating determination results of the three conditions explained above.

Note that, in the example shown in FIG. 21, all the intersection line segments 31s configuring the shape cross section 31c are present in the region EP. The polygon 31p including all the intersection line segments 31s is determined as an erroneous estimation portion.

Thereafter, the display-form changing section 23c of the three-dimensional-image generating section 23 selects the polygon 31p determined as the erroneous estimation portion (step S53).

The display-form changing section 23c changes a display color of the selected polygon 31p to a color different from a display color of the polygon 31p not determined as the erroneous estimation portion (step S54). In this way, a three-dimensional image in which the erroneous estimation portion has the different color is displayed on the display apparatus 4.

After performing the processing in step S54 explained above, the endoscope system returns to the processing shown in FIG. 18.

In this embodiment, instead of changing the erroneous estimation portion to the different color by the display-form changing section 23c, the erroneous estimation portion may be deleted by the shape correcting section 23b. Similarly, in the embodiments explained above or embodiments explained below, the erroneous estimation portion may be either deleted or changed to the different color.

According to such a fourth embodiment, substantially the same effects as the effects in the first embodiment explained above are also achieved by determining, as an erroneous estimation portion, a pair of polygons 31p in which an angle formed by the projected normal vectors 34 is equal to or larger than the angle threshold θ2th, a linear distance between the center points 31a is smaller than the first threshold L1th, and a distance along the shape cross section 31c between the center points 31a is equal to or larger than the second threshold L2th.

Further, by displaying the erroneous estimation portion in a display form (for example, a display color) different from that of the other portions in the three-dimensional shape 31 and warning the user, the user is capable of recognizing the erroneous estimation portion at a glance. It is possible to improve reliability of the estimated three-dimensional shape 31 in the subject.

Fifth Embodiment

Figure 22:
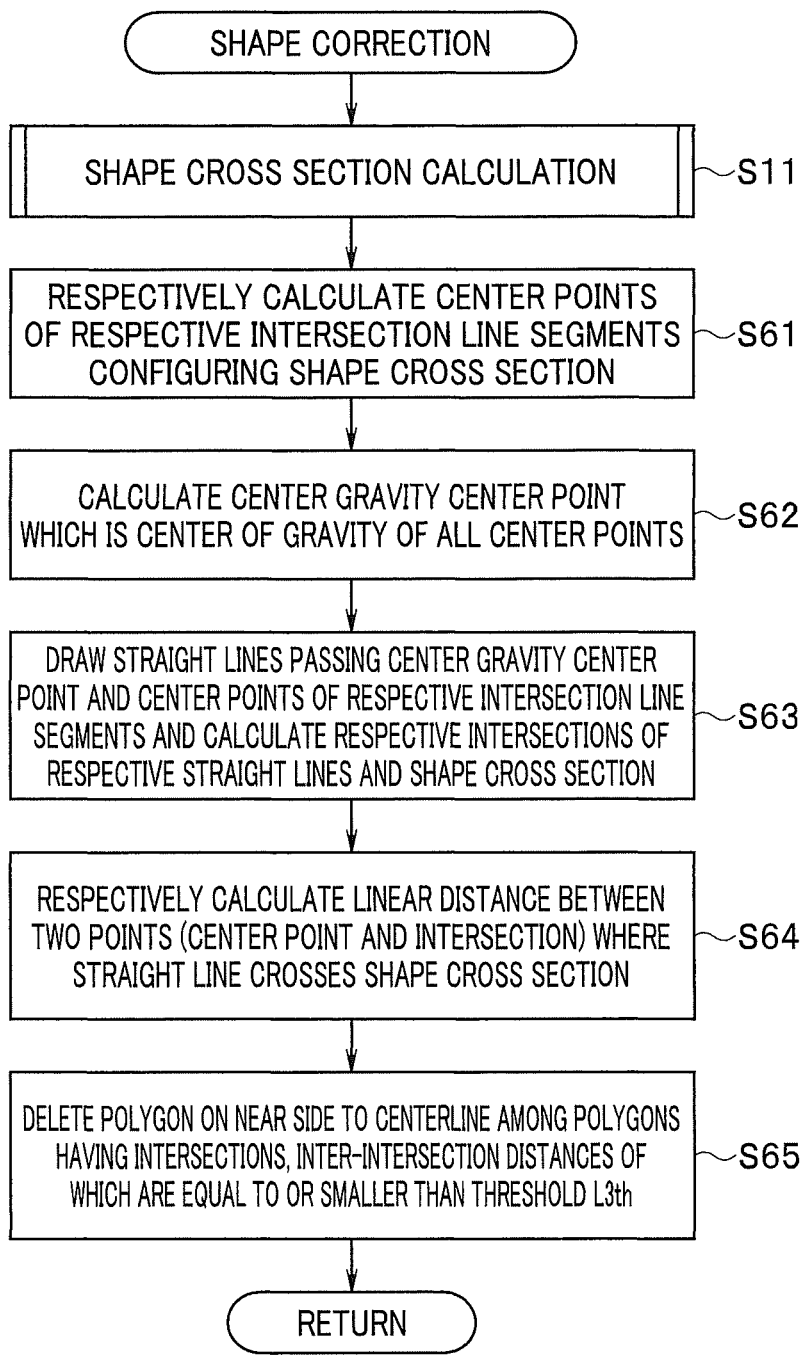
FIG. 22 is a flowchart showing processing of shape correction in a fifth embodiment of the present invention.
Figure 23:
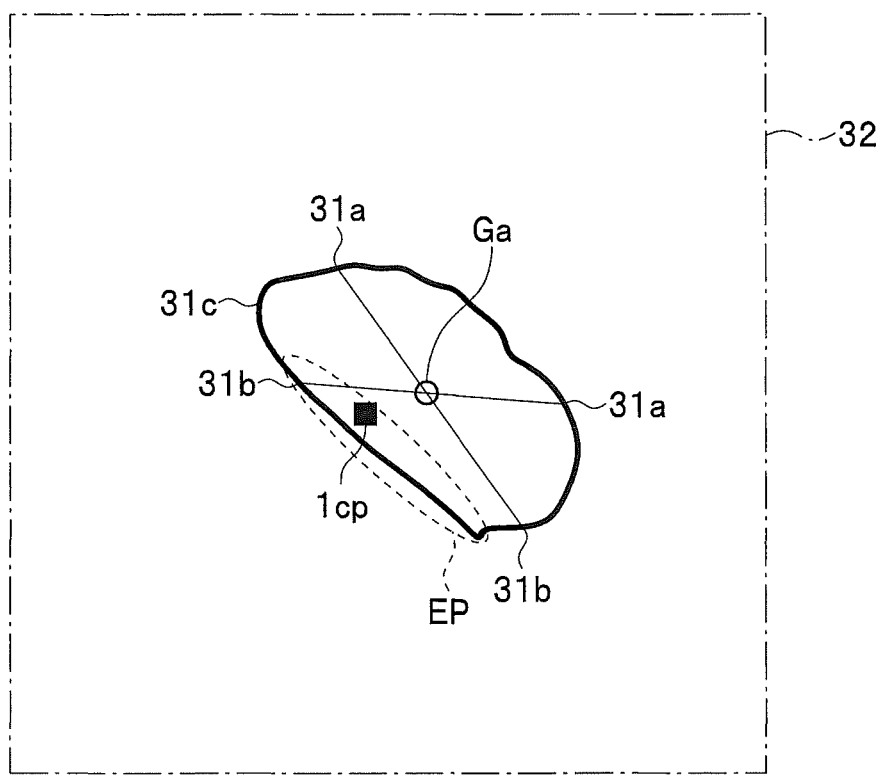
FIG. 23 is a diagram showing an example of a region of a polygon close to a point where a centerline and a cross section cross when a linear distance between two points where a straight line passing a center gravity center point crosses a shape cross section is equal to or smaller than a threshold.

FIG. 22 and FIG. 23 show a fifth embodiment of the present invention. FIG. 22 is a flowchart showing processing of shape correction.

In the fifth embodiment, the same portions as the portions in the first to fourth embodiments explained above are denoted by the same reference numerals and signs and explanation of the portions is omitted as appropriate. Only differences are mainly explained.

In the first and second embodiments explained above, the determination of an erroneous estimation portion is performed based on the trajectory center of gravity point Gt. In the third embodiment explained above, the determination of an erroneous estimation portion is performed based on the trajectory point Pt. On the other hand, in the fifth embodiment, the determination of an erroneous estimation portion is performed based on a point 1cp where the centerline 1c crosses the cross section 32.

When entering processing shown in FIG. 22 in step S7 in FIG. 5, in step S11, the endoscope system calculates the shape cross section 31c.

Subsequently, the determining section 27 respectively calculates the center points 31a of all the intersection line segments 31s configuring the shape cross section 31c (step S61).

Subsequently, the determining section 27 calculates a center gravity center point Ga (see FIG. 23), which is a center of gravity of all the center points 31a (step S62).

Further, the determining section 27 generates, with respect to each of the plurality of intersection line segments 31s, straight lines passing the center gravity center point Ga and the center points 31a of the respective intersection line segments 31s and calculates respective intersections of the respective straight lines and the shape cross section 31c (step S63). When the shape cross section 31c is formed in a closed curve, the straight lines and the shape cross section 31c have at least two intersections. One of the two intersections is the center point 31a. Further, when the shape cross section 31c is a closed curve convex to an outer diameter side similar to a circle or an ellipse, the center gravity center point Ga is assumed to be present on the inner side of the shape cross section 31c. Therefore, for example, the determining section 27 calculates an intersection 31b (see FIG. 23) present on an opposite side of the center point 31a across the center gravity center point Ga.

The determining section 27 respectively calculates, with respect to the respective straight lines, a linear distance between two points of the straight lines crossing the shape cross section 31c (an inter-intersection distance, more specifically, a linear distance between the center point 31a and the intersection 31b present on the opposite side of the center point 31a across the center gravity center point Ga) (step S64).

FIG. 23 is a diagram showing an example of the region EP of the polygon 31p close to the point 1cp where the centerline 1c and the cross section 32 cross when a linear distance between two points where a straight line passing the center gravity center point Ga crosses the shape cross section 31c is equal to or smaller than a threshold L3th.

Thereafter, the determining section 27 determines, as an erroneous estimation portion, of two polygons 31p respectively having two intersections crossing a straight line, an inter-intersection distance of which is equal to or smaller than the threshold L3th, (the polygon 31p having the center point 31a and the polygon 31p having the intersection 31b), the polygon 31p closer to the point 1cp where the centerline 1c and the cross section 32 cross (the polygon 31p including the intersection line segment 31s shown in the region EP in FIG. 23). Note that an example of a value of the threshold L3th is approximately a double of a diameter of the insertion section of the endoscope 1. However, the value of the threshold L3th is not limited to this. Any appropriate value may be used. The shape correcting section 23b in the three-dimensional-image generating section 23 deletes the polygon 31p determined as the erroneous estimation portion by the determining section 27 (or may differentiate the display form and warn the user as explained above) (step S65).

After performing the processing in step S65 in this way, the endoscope system returns to the processing shown in FIG. 5.

According to such a fifth embodiment, substantially the same effects as the effects in the first embodiment explained above are achieved. Further, of two polygons 31p each having an intersection at which a straight line passing the center gravity center point Ga intersects with the shape cross section 31c, a distance of the intersections being equal to or smaller than the threshold L3th, the polygon 31p closer to the centerline 1c (the point 1cp) is determined as an erroneous estimation portion. Therefore, the polygon 31p closer to the distal end portion of the endoscope 1 of the two polygons 31p can be appropriately determined as the erroneous estimation portion.

Note that, in the above explanation, the present invention is the endoscope system. However, the present invention is not limited to this. The present invention may be a processor for endoscope alone, may be an operation method for operating the endoscope system as explained above, or may be a processing program for causing a computer to perform the same processing as the processing of the endoscope system, a computer-readable non-transitory recording medium that records the processing program, and the like.

Further, the present invention is not limited to the embodiments explained above per se. In an implementation stage, the constituent elements can be modified and embodied in a range not departing from the gist of the present invention. Various forms of inventions can be formed by appropriate combinations of the plurality of constituent elements disclosed in the embodiments. For example, several constituent elements may be deleted from all the constituent elements explained in the embodiments. Further, the constituent elements in the different embodiments may be combined as appropriate. In this way, it goes without saying that various modifications and applications are possible within the range not departing from the gist of the invention.

What is claimed is:

1. An endoscope system comprising:
    an endoscope that picks up an image in a subject and acquires the image; and
    a processor, wherein the processor
    acquires position information and posture information of the endoscope,
    estimates, based on the image, a relative three-dimensional position viewed from the endoscope of a target portion in the subject,
    estimates a three-dimensional shape in the subject based on the relative three-dimensional position and the position information and the posture information,
    generates a cross section, which is a plane crossing a centerline of a region including a trajectory on which the endoscope passed, based on the position information, and
    determines an erroneous estimation portion in the three-dimensional shape based on a shape characteristic of a shape cross section, which is a portion crossing the cross section, of the three-dimensional shape.

2. The endoscope system according to claim 1, wherein
    the processor estimates the three-dimensional shape as a shape obtained by connecting a plurality of polygons,
    the shape cross section is formed in a polygonal line obtained by connecting a plurality of intersection line segments, which are intersection lines of the cross section and the polygons, and
    the processor determines, based on each of the intersection line segments, whether the polygon including the intersection line segment is the erroneous estimation portion.

3. The endoscope system according to claim 2, wherein the processor generates, with respect to each of the plurality of intersection line segments, a connecting line segment having, as both ends, a trajectory point that is an intersection of the cross section and the trajectory, and a center point of the intersection line segment and determines, as the erroneous estimation portion, the polygon including the intersection line segment crossing the connecting line segment in a part other than both the ends of the connecting line segment.

4. The endoscope system according to claim 3, wherein, when the trajectory point in plurality is present on one cross section, the processor generates the connecting line segment with one end set at a trajectory center of gravity point that is a center of gravity of the plurality of trajectory points, and determines the erroneous estimation portion.

5. The endoscope system according to claim 3, wherein, when the trajectory point in plurality is present on one cross section, the processor generates the connecting line segment with respect to each of the plurality of trajectory points and determines the erroneous estimation portion.

6. The endoscope system according to claim 2, wherein the processor generates, with respect to each of the plurality of intersection line segments, a center vector from a trajectory center of gravity point to a center point of the intersection line segment, the trajectory center of gravity point being a center of gravity of a trajectory point that is an intersection of the cross section and the trajectory, generates, with respect to each of the polygons including the intersection line segments, projected normal vectors obtained by projecting normal vectors of the polygons onto the cross section, and determines, as the erroneous estimation portion, the polygon including the intersection line segment in which an angle formed by the center vector and the projected normal vector is equal to or larger than an angle threshold.

7. The endoscope system according to claim 2, wherein the processor generates, with respect to each of the polygons including the intersection line segments, projected normal vectors obtained by projecting normal vectors of the polygons onto the cross section, and determines, as the erroneous estimation portion, a pair of the polygons in which an angle formed by the projected normal vectors is equal to or larger than an angle threshold, a linear distance between center points of the intersection line segments is smaller than a first threshold, and a distance along the shape cross section between the center points of the intersection line segments is equal to or larger than a second threshold that is larger than the first threshold.

8. The endoscope system according to claim 2, wherein the processor calculates a center gravity center point, the center gravity center point being a center of gravity of center points of all the intersection line segments configuring the shape cross section, generates, with respect to each of the plurality of intersection line segments, straight lines passing the center gravity center point and the center points of the intersection line segments, and determines, as the erroneous estimation portion, a polygon closer to the centerline of a pair of the polygons crossing the straight lines, a linear distance between two points where the straight lines cross the shape cross section being equal to or smaller than a threshold.

9. The endoscope system according to claim 1, wherein the processor generates, along the centerline, at every constant interval, a plurality of cross sections perpendicular to the centerline.

10. The endoscope system according to claim 1, wherein the processor deletes the erroneous estimation portion from the three-dimensional shape.

11. The endoscope system according to claim 1, wherein the processor displays the erroneous estimation portion in a display form different from a display form of other portions in the three-dimensional shape.

12. A processor for an endoscope that
acquires position information and posture information of an endoscope,
estimates, based on an image acquired by the endoscope, a relative three-dimensional position viewed from the endoscope of a target portion in a subject,
estimates a three-dimensional shape in the subject based on the relative three-dimensional position and the position information and the posture information,
generates a cross section, which is a plane crossing a centerline of a region including a trajectory on which the endoscope passed, based on the position information, and
determines an erroneous estimation portion in the three-dimensional shape based on a shape characteristic of a shape cross section, which is a portion crossing the cross section, of the three-dimensional shape.

13. An operation method for an endoscope system, the endoscope system including an endoscope that picks up an image in a subject and acquires the image, the operation method comprising:
acquiring position information and posture information of the endoscope;
estimating, based on the image, a relative three-dimensional position viewed from the endoscope of a target portion in the subject;
estimating a three-dimensional shape in the subject based on the relative three-dimensional position and the position information and the posture information;
generating a cross section, which is a plane crossing a centerline of a region including a trajectory on which the endoscope passed, based on the position information; and
determining an erroneous estimation portion in the three-dimensional shape based on a shape characteristic of a shape cross section, which is a portion crossing the cross section, of the three-dimensional shape.

* * * * *